US008921646B2

(12) United States Patent
Wilson et al.

(10) Patent No.: US 8,921,646 B2
(45) Date of Patent: Dec. 30, 2014

(54) GENETIC LOCI ASSOCIATED WITH NORTHERN LEAF BLIGHT RESISTANCE IN MAIZE

(75) Inventors: William A. Wilson, Noblesville, IN (US); Bailin Li, Hockessin, DE (US); Stanley Luck, Wilmington, DE (US); Marymar Goncalves Butruille, Des Moines, IA (US)

(73) Assignees: E. I. du Pont de Nemours and Company, Wilmington, DE (US); Pioneer Hi-Bred International, Inc., Johnston, IA (US)

( * ) Notice: Subject to any disclaimer, the term of this patent is extended or adjusted under 35 U.S.C. 154(b) by 1224 days.

(21) Appl. No.: 12/577,837

(22) Filed: Oct. 13, 2009

(65) Prior Publication Data

US 2010/0095395 A1    Apr. 15, 2010

Related U.S. Application Data

(60) Provisional application No. 61/104,804, filed on Oct. 13, 2008.

(51) Int. Cl.
| | |
|---|---|
| *A01H 1/04* | (2006.01) |
| *A01H 1/02* | (2006.01) |
| *A01H 5/10* | (2006.01) |
| *C12N 15/82* | (2006.01) |
| *C12Q 1/68* | (2006.01) |

(52) U.S. Cl.
CPC ........ *A01H 1/04* (2013.01); *C12N 15/82* (2013.01); *C12Q 1/6895* (2013.01)
USPC ........... 800/267; 800/265; 800/266; 800/275; 800/300.1; 435/6.11

(58) Field of Classification Search
None
See application file for complete search history.

(56) References Cited

PUBLICATIONS

Ogliari et al. Genetic and Molecular Biology 28(3): 435-439, 2005.*
Gupta et al., 1989. Identification of RFLP markers for the Ht1 gene by comparison of inbreds and their Ht1-conversions. MNL, vol. 63:112.
Bentolila et al., 1991. Identification of an RFLP marker lightly linked to the Ht1 gene in maize. Theor Appl Genet, vol. 82:393-398.
Li et al., 1998. The physical location of the gene ht1 (*Helminthosporium turcicum* resistance1) in maize (*Zea mays* L.). Hereditas, vol. 129:101-106.
Has et al., 2006, Effects of the Ht1 or Ht2 gene in five maize inbred lines on quantitative resistance to *Exserohilum turcicum* , MNL, vol. 80:29.
Wisser et al., 2008. Selection mapping of loci for quantitative disease resistance in a diverse resistance in a diverse maize population. Genetics, vol. 180(1):583-599.
Zuping et al., 2007. QTL mapping for resistance to northern corn leaf blight in maize. Southwest China Journal of Agricultural Sciences, vol. 20(4):634-637.
Brown et al., 2001. Quantitative trait loci in sweet corn associated with partial resistance to Stewart's wilt, northern corn leaf blight, and common rust. Phytopathology, vol. 91(3):293-300.
Welz and Geiger, 2000. Genes for resistance to northern corn leaf blight in diverse maize populations Plant Breeding vol. 119(1):1-14.
Welz et al., 1999. QTLs for resistance to *Setosphaeria turcica* in an early maturing DentxFlint maize population. Theoretical and Applied Genetics, vol. 99(3/4):649-655.
Welz et al., 1999. Dynamic gene action at QTLs for resistance to *Setosphaeria turcica* in maize. Theoretical and Applied Genetics, vol. 98(6/7):1036-1045.
Schechert et al., 1999. QTL for resistance to *Setosphaeria turcica* in tropical African maize. Crop Science, vol. 39(2):514-523.
Moon et al., 1999. Major QTLs for disease resistance and other traits identified in recombinant inbred lines from tropical maize hybrids. Maydica, vol. 44(4):301-311.
Dingerdissen et al., 1996. Interval mapping of genes for quantitative resistance to *Setosphaeria turcica*, cause of northern leaf blight, in tropical environment. Molecular Breeding, vol. 2(2):143-156.
Khampila et al., 2008. Identification of RAPD and SCAR markers linked to northern leaf blight resistance in waxy corn (*Zea mays* var. *ceratina*). Euphytica, vol. 164(3):615-625.
Qinghua et al., 2002. Progress of DNA molecular marker technique for northern corn leaf blight. Journal of Maize Sciences, vol. 10(2):96.
Asea et al., 2009. Validation of consensus quantitative trait loci associated with resistance to multiple foliar pathogens of maize. Phytopathology, vol. 99(5):540-547.
Khampila et al., 2008. Identification of RAPD markers for northern corn leaf blight resistance in waxy corn (*Zea mays* var. *ceratina*). Euphytica, vol. 164(3):615-625.
Collins et al., 1998. The isolation and mapping of disease resistance gene analogs in maize. Molecular Plant-Microbe Interactions, vol. 11(10):968-978.
Coe, E.H. et al., 1988. Corn and Corn Improvement, 3rd ed., pp. 81-258.

* cited by examiner

*Primary Examiner* — Brent T Page
*Assistant Examiner* — Jared Shapiro

(57) ABSTRACT

The invention relates to methods and compositions for identifying and selecting maize plants with enhanced resistance to *Exserohilum* and/or northern leaf blight. Maize plants generated by the methods of the invention are also a feature of the invention.

2 Claims, 4 Drawing Sheets

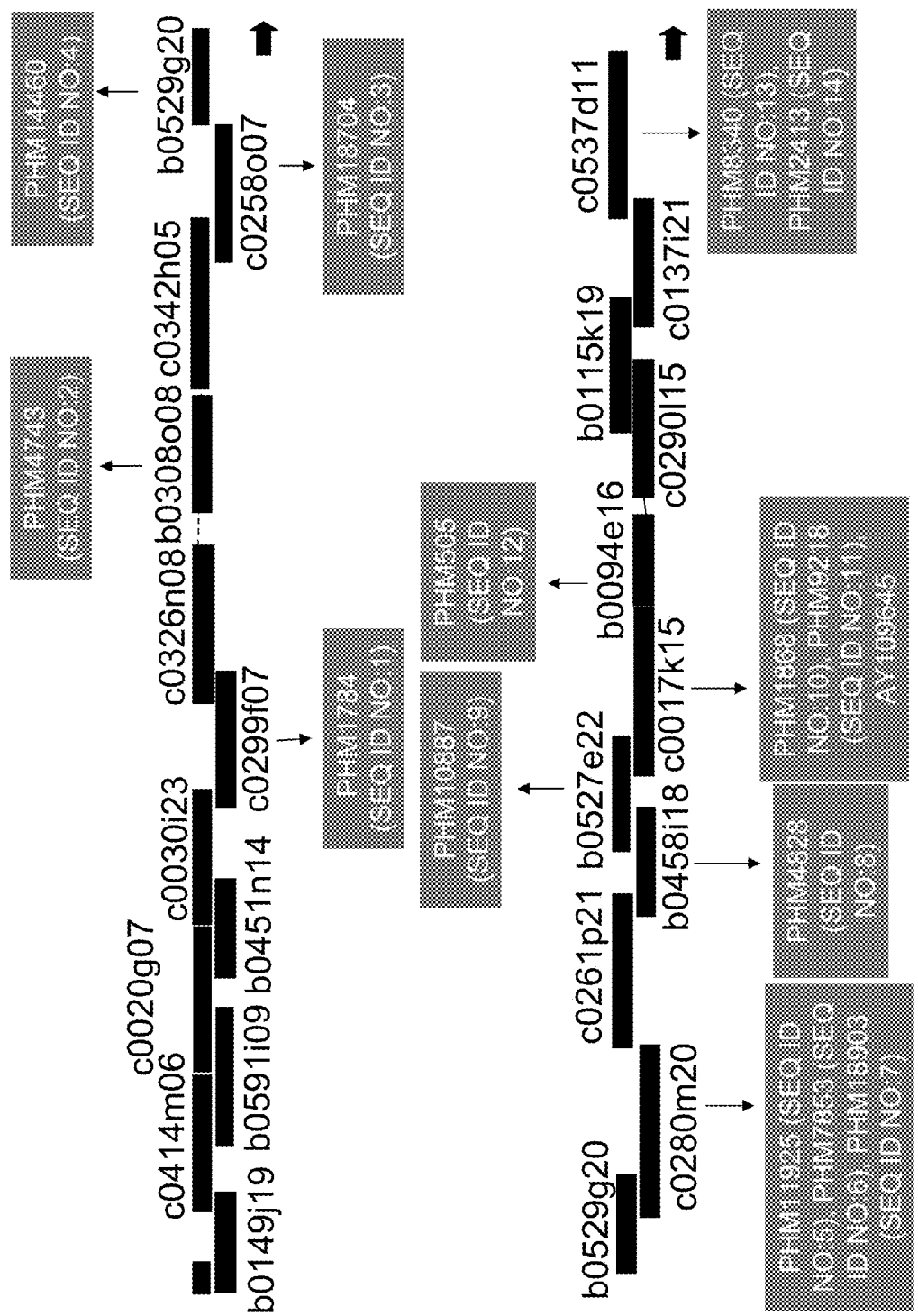
FIG. 1A: Physical map

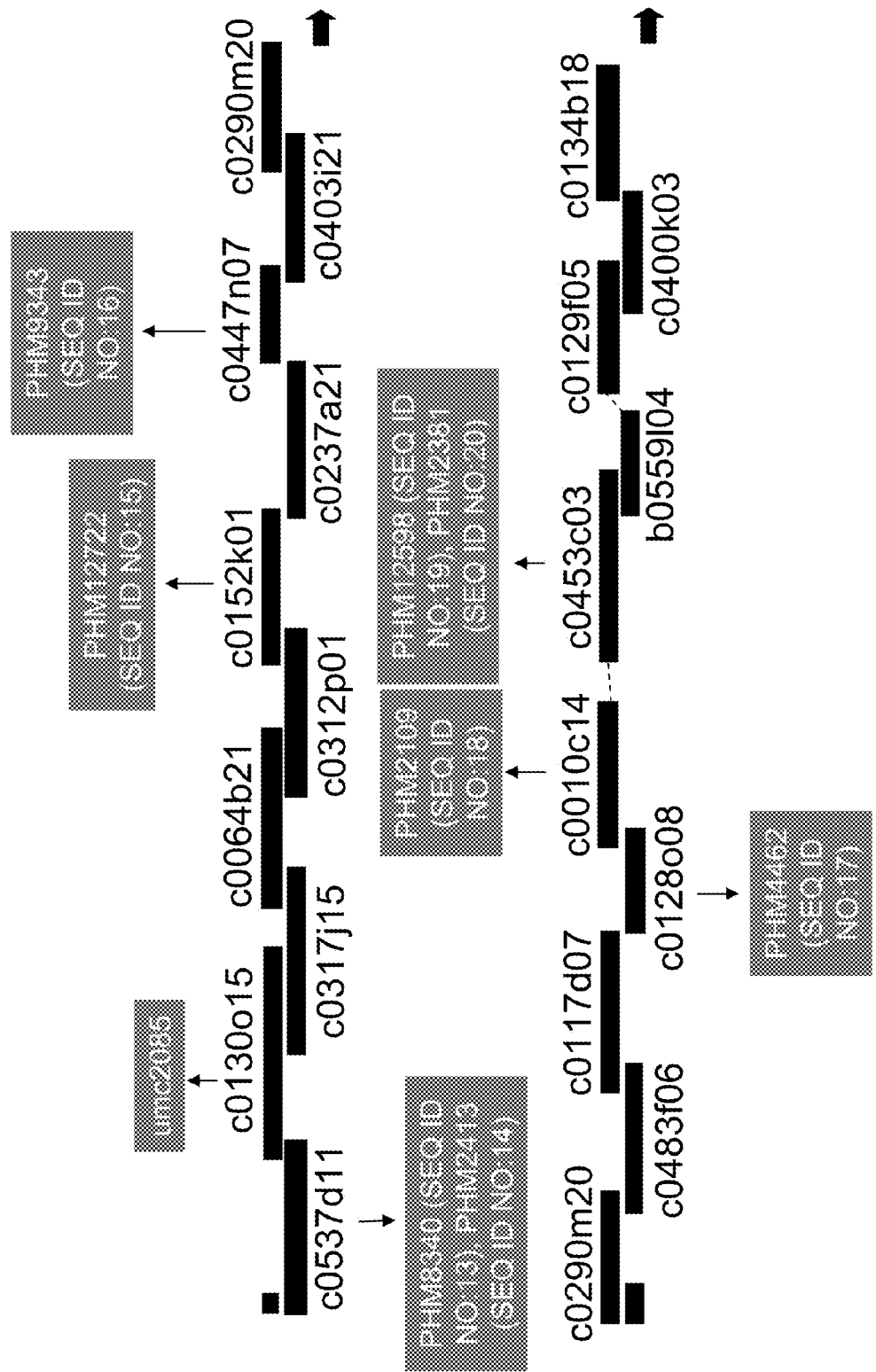
FIG. 1B: Physical map (cont.)

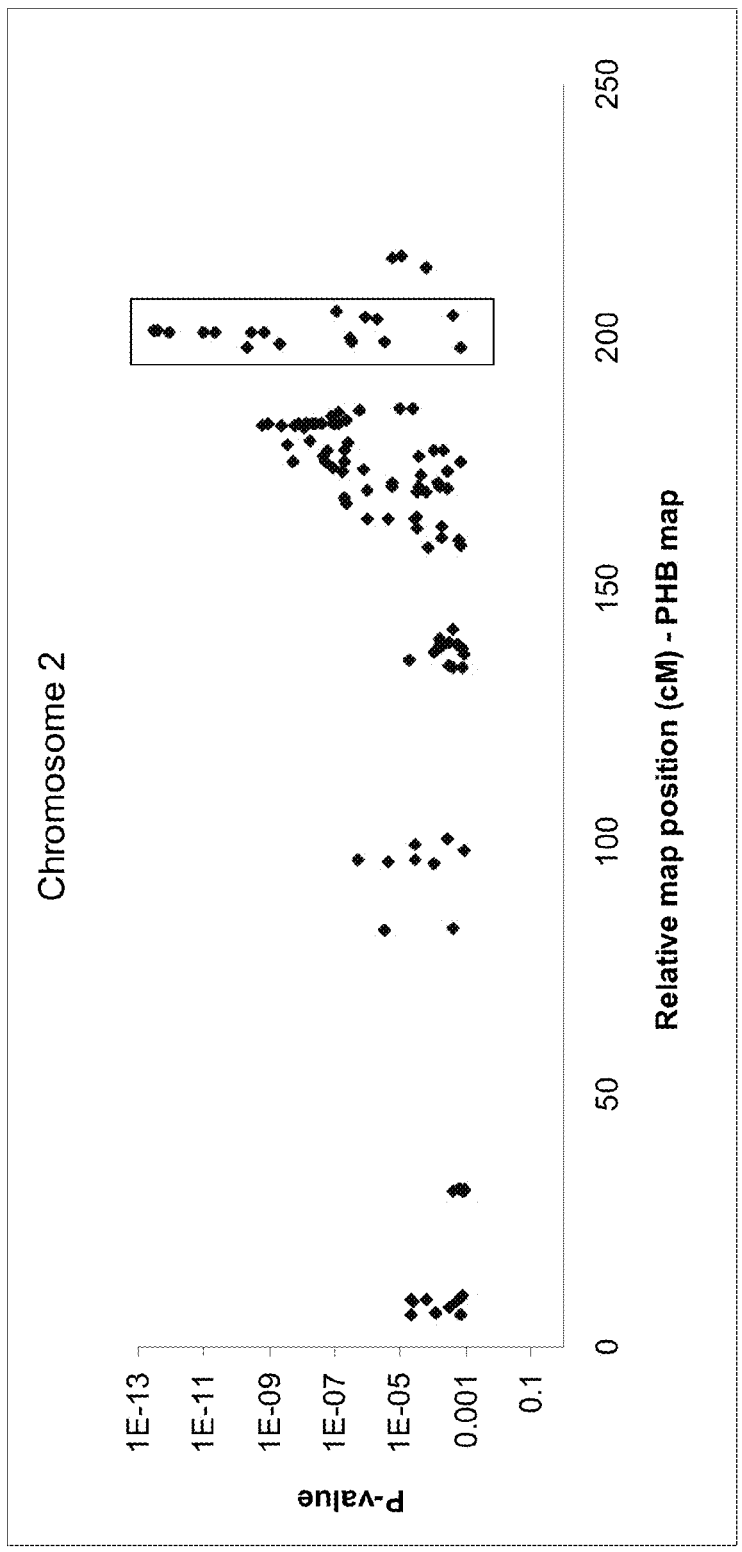
FIG. 2: Associations between marker loci on chromosome 2 and northern leaf blight resistance in a stiff stalk subpopulation at p ≤ 0.001. The lines used in the association analysis had phenotypic scores of 1 and 9.

FIG. 3 Scoring guide for northern leaf blight infection in maize
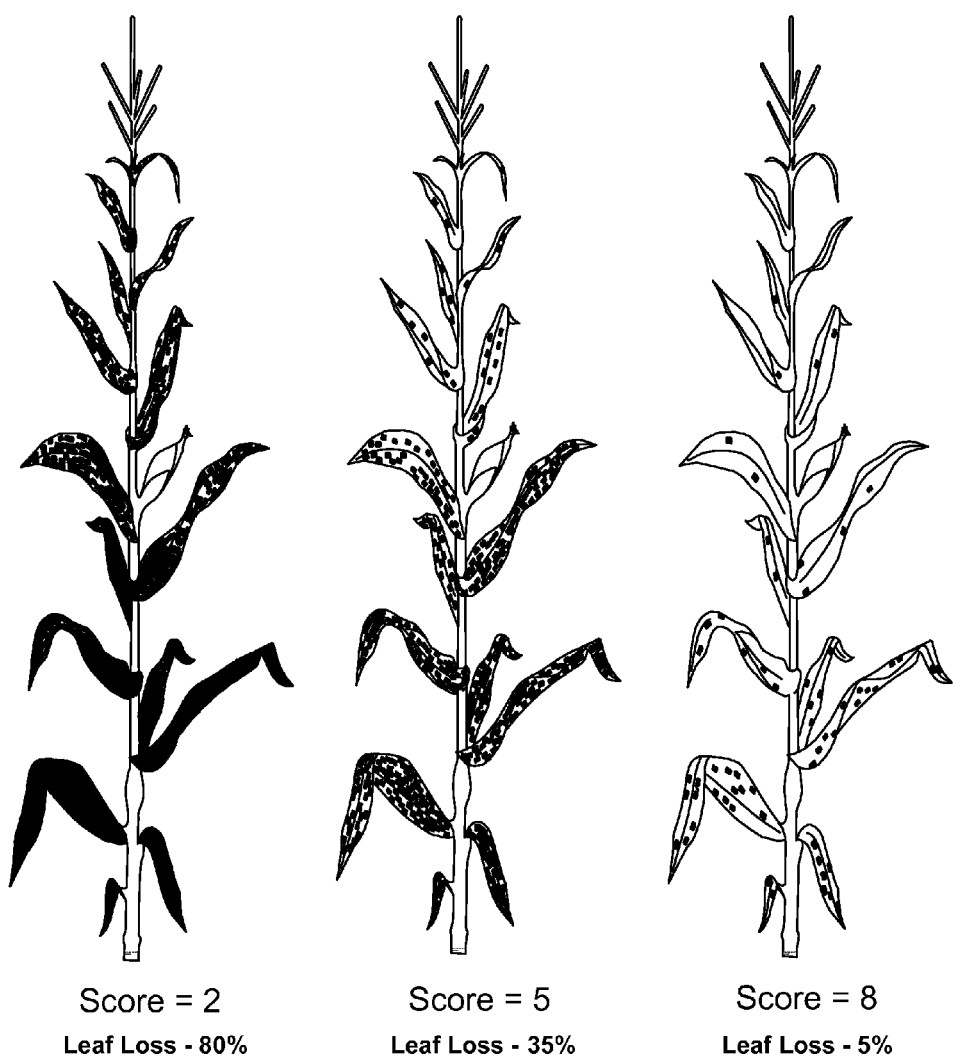

SEQUENCE LISTING

<160> NUMBER OF SEQ ID NOS: 132

<210> SEQ ID NO 1
<211> LENGTH: 634
<212> TYPE: DNA
<213> ORGANISM: Artificial
<220> FEATURE:
<223> OTHER INFORMATION: PHM1784 reference sequence

<400> SEQUENCE: 1

```
tgcgatctac tctccccata caaagaaaag gatatgggaa ttcctgattg cttctgtaag      60
tatggctgtt gatgttgtat gttccatttt atgatcatta agtttgaat atcttgtggg     120
acaaatagta ctttaggcat tttattcact gaagaactgt ttttgctgtt gtagcatatg    180
aactttccaa gaaagaaggt aaagttggga caccggagcg ccctctctct gatcttggtc    240
tgctcagcta tagaggttat tggactagag tgcttctgga aattctaaag aaacataagg    300
gaaacatatc tataaaggta acacccttcc atccagatat acctttttcg ttgtacaaat    360
ttcgaaagct gattgaatta tgatgcagca gttctagaaa gaaactttct attggctcct    420
cgtattaccc tacttaaccc ttggtctatg acaaaaaagg gttaccctg tgtttcatag    480
attacactc aataagcagg gggattttct gagctgcaat tgcgcgttag tcaaacattc    540
cctaaataag tagtcttcta gaacataatg tatggtaatg gtcttttggg atgaaaaaga    600
tccctcagg aatttttggg tttatccagt tcca                                634
```

<210> SEQ ID NO 2
<211> LENGTH: 699
<212> TYPE: DNA
<213> ORGANISM: Artificial
<220> FEATURE:
<223> OTHER INFORMATION: PHM4743 reference sequence

<400> SEQUENCE: 2

```
aaactgactg tttatttca tgcaatgggt ttccatcggt acactgtcga aaaccttaaa      60
gacgtttcat cagacgctct gttggaccgt gaagtggaag aatttgaccc accgtccgag    120
gtttgcgaag aggaatattg tatcagttta tatgatatct tgtcaagcag attgccatgc    180
ttatgctgaa catcgcctgc ctgtaggttc gtgccatcat tgagggccaa atgctgtcga    240
tgcgaggcca cgccgagagg tttggcatgc cgaaccctcc caaacggatc atagcaaccg    300
gcggggcatc ctccaacgaa agcatcctca agtcagtcgc gcagatcttc ggttgccctg    360
tcttcacagt ccagagacct ggtaatcgct caaatctcct actccctgaa cgaacttggt    420
tgtccaatcc aacttgtcct ggcacaaatc tgatggcact ataatatcgc tgctgaactg    480
acgctgtccc tgtctgtcca tgaccagatt cggcatcgct gggcgcagcg ctgagagctg    540
cccacgggtg gctatgcaac gcgcaaggta gcttcgtccc catctcgtgc ctgtaccagg    600
gcaacctgga gaagacctcc cttggctcga aggagcagtc ccggccggcg acaaggagca    660
ggaccggagc tcctccagag tcaccaactt gtaagtaaa                           699
```

<210> SEQ ID NO 3
<211> LENGTH: 500
<212> TYPE: DNA
<213> ORGANISM: Artificial
<220> FEATURE:
<223> OTHER INFORMATION: PHM18704 reference sequence

<400> SEQUENCE: 3

```
gaagcacccc cattggtaaa gttgtggtgg tagatgatta tgcaatcaag gcataaagcg      60
```

```
gttcagaagg actatggcat tttgttcagg cagtacgcag tacagtgatg cctgatgctg    120
gtggttatga tctgctctca ttgtacccag atggcttaaa aggcttccat gaaatatgag    180
ttgacatcga ggaaattttc tgtagtattg gtatagtttc atagctgttg ctactgattg    240
aagactcgag ctatccatat tgtattccca gtttctactt gcagcaagca tggctgtgaa    300
gttaagtgta tccactttg aagcatgacg agagagtctg aaatgcaagc aaactgcatt     360
aaagacagtc atgctgttgg ctgcaaggtt acctatagtt tggttacctc ttgtctccgt    420
tgggaaaggt ttggagttcc atctaaagca cctttcagca tctttgctcc catcttaatg    480
gtcatagctg tcctttcccc                                                500
```

<210> SEQ ID NO 4
<211> LENGTH: 665
<212> TYPE: DNA
<213> ORGANISM: Artificial
<220> FEATURE:
<223> OTHER INFORMATION: PHM14460 reference sequence

<400> SEQUENCE: 4

```
accgaaaagg gtttccggct ttgggagttc gggggcaact ttaactttcg gttcccggaa     60
ggagcaggcc attttttgaga ttgggggcaa catttgggc cccgcaaaca acacggccg    120 cgatccctcg gctgactccg acgatgaaga cgccgccgcc gccgccgcga cacagatacc    180
tgccaacacc agccccaacg agaagtcag gtccccgtcc tctgcacggc agcgtcgccg    240
caggcgggcg acggaattga cccctgccac aaacatgttg cagcccccctc agccagtgcc    300 actgtctgtg tcagtgcctg tcaagacgga tgactccctc ccagcacagc cccagacccc    360
aatgccgacc atggatggct cagagcctgt caggttgcca gtcgtgtcgc ctcaatcagg    420
agtttctgat gccgagaaga cttgcctgac tcctctattt agggagataa tacatgcagc    480
gatgaatgtc ggagcaaacc catttggtgc aaagctgcct gagccgccgc ttgggttgcc    540
cttgcccatg gaagggagga gtggcggag gcagcggatt ttggagctgg aggtctactt    600
gaagaggatc gagctgctgc aggatcaggc gaagcaacgc ttgagagctc gaaatgggga    660
aaaaa                                                                665
```

<210> SEQ ID NO 5
<211> LENGTH: 526
<212> TYPE: DNA
<213> ORGANISM: Artificial
<220> FEATURE:
<223> OTHER INFORMATION: PHM11925 reference sequence

<400> SEQUENCE: 5

```
agaagggaag gtcccagtca aaacgttgat ggcgtactca ttgttttgct gcctaagttt     60
ggtttgcgtg tacaagctag aatttaaaca ataaaagcat gcaggtggca aaaagtcatg    120
aagaagccct ctgatgaacc agctgtatcc gaccatatct gacaagttat tagtatcagc    180
cactagcacg tgtgtgaatt tcagcaggac catactagtt agcaaagtag caaactacta    240
tcagtggcac tgggtaaata actactttgg ctgttgatat ccttgagcag ttgaggatta    300
agcagttgtc cagcatgaac cagcaagcca acataaact attcaacttc cattattatt     360
gtcaaaaaag aaataatgat gagtaaaagg tattcaaatt cattgcctgg ttcacttttg    420
tagtcatgca caatatggaa tgaaataggc atcaatactc gatgtttcca aatctgttgt    480
ccatataatt cataactcat gtaattgggt attaaagggg ggtgta                   526
```

<210> SEQ ID NO 6
<211> LENGTH: 705
<212> TYPE: DNA
<213> ORGANISM: Artificial
<220> FEATURE:
<223> OTHER INFORMATION: PHM7853 reference sequence

<400> SEQUENCE: 6

```
aagttactga ggaaaaaaat gcggcagcag tgctgataat gccagttctt aggattttcg      60
gattcagggt ttgcactaaa gcttgcattg ctcggaaacc tgacatcgga atcataccttt     120
gtatccaatc attggtcata gcttctggct agctgtttgg gactgaattg cttctatcga     180
gtgcatagtg cgtgacattg cagataagac tattgactaa ttaacctcgc ctcgcaaaca     240
ggcatttcaa ggaagacaac tgagggtgaa ctgcgggcca ccgccaccta gagatgaatc     300
cacaccaaga gcaccaaggg gtggtggtgg cggcggcggc ggcggctttg tcgattcagc     360
taacaaggtc tacgtgggga accttgcgtg gggcgttgac aactcgactc tggagaacct     420
gttcagtgag caagggcaag tgcttgatgc taaggtcatc tacgacaggg atagcggcag     480
gtcaaggggg tttggtttcg tcacctatgg ctccgcccaa gaggtcaaca atgccatatc     540
aaacctcgat ggcatcgtaa gttctatgct attttgatcc tttagcgcat tgttgtacat     600
agaggatgtg ctaatctgaa tgttttatcg taatgcagga cttggatggt agacagatcc     660
gagtcacggc tgcgagtcaa agccgaactc atccttgcgg ttatt              705
```

<210> SEQ ID NO 7
<211> LENGTH: 731
<212> TYPE: DNA
<213> ORGANISM: Artificial
<220> FEATURE:
<223> OTHER INFORMATION: PHM18903 reference sequence

<400> SEQUENCE: 7

```
gaggaaaggc ccagtaaaaa gtccttcgtc tctcagggta atagatattc agggttgctt      60
caaactacgg ctcatgtcag ggcagctgga tgcactcaat accttagcaa tcaccaactg     120
cccggagttg cgatcactgg aaacatgcat cgtagatctc acgtcactgg aaatcctcgc     180
tctgtgtggt tgcaaaagct ggcgtccttt gcctagttcg tgggcaggac gacaagaata     240
ttcatctctc cgtcagctta cgattaggga gtgcccaggt ataaaatcgt tgccttcaac     300
tctgcagcag cgactggaca acggcctctt ggattttacg aacctagatt cccgtcgtcg     360
tgaaggtacg caccaatctt gtgcttatcc acagcatgcc tctgaaatcc agcatgccag     420
ttaattccct atgttgctca ttcaatagag tctgtcgaca actttggaag caaagttcgg     480
ccgaattagc atgtgtttaa agttttattg agattaatcg taatttatta tgagtaattt     540
tccttcaatt aatatattcg gcaatcctct tgccgtcctt tcgaaaaaaa atcttgtgct     600
tatccacagc atgcctctga aatccagcat gccagttaat tccctatgtt gctcattcaa     660
tagagtctgt cgacaacttt ggaagcaaag ttcggccgaa ttagcatgtg tttaaagttt     720
tatgagatta t                                                          731
```

<210> SEQ ID NO 8
<211> LENGTH: 512
<212> TYPE: DNA
<213> ORGANISM: Artificial
<220> FEATURE:
<223> OTHER INFORMATION: PHM4828 reference sequence
<220> FEATURE:
<221> NAME/KEY: misc_feature
<222> LOCATION: (5)..(5)
<223> OTHER INFORMATION: n is a, c, g, or t

<400> SEQUENCE: 8

| | | |
|---|---|---|
| atcanccttg tttaaaacat atatgaggat aaacttgttg cttttttgtg atgcaattga | 60 |
| gaaaactttc gaatttgaac tggttcccaa tattttgttc tccctgtccc ctgttgaagt | 120 |
| gctctctgtt ttaagttagc aattaacggc atcggattta cttgtgaacc tttgcacgat | 180 |
| ccatcaaagg cgaaggcagc agctgggcat gccgctcaat ctgattatcg gtgctgttca | 240 |
| actgaagatg gcgcatgatc ccgcatacgg gttgcctggt tcggttgcta gcccacccac | 300 |
| gtccctacac aaggctgtcc ggctgctgca ttgcagcgct gttgctgctg aagtgcactg | 360 |
| ttgctaacaa gcagctgaag ggattttcag ccgcagtcga tcggcagctg cagtggctgt | 420 |
| ttagccctgt gtggatagct acatctctaa aaaatttggt ggagctggag ttttaagcta | 480 |
| gaatcagaat atggtcatag ctgtcccttc cc | 512 |

<210> SEQ ID NO 9
<211> LENGTH: 675
<212> TYPE: DNA
<213> ORGANISM: Artificial
<220> FEATURE:
<223> OTHER INFORMATION: PHM10887 reference sequence

<400> SEQUENCE: 9

| | | |
|---|---|---|
| gcgcggtgtc ccccggggga gcgcccagga cacccagcag ctcaagccag gccgcagccg | 60 |
| gctgcgtccg aggtgagcgt ttcgtgcctc cgtcgttaaa aaccgtacgt gctgatccga | 120 |
| atctgatcgc cgcgaagtct ggttgtctga gttccgctcg atctgtctgc agaaaccggc | 180 |
| ggctcaactc gacgcgaact ctgtgcgagc gaagctggag ctcgcgaaga acgccaagct | 240 |
| cgaggcgacc aagaggaagc tccaggaagg gtaccaagaa tccgataacg gtatgcgtgc | 300 |
| tgctgctgct gctcctgctc ctatgggtat aggatatcca tccttcattg tgctggtggt | 360 |
| ggttcatgca ttgtgctgtg ctgcttgatg gaccgagaat ctgatctcca tttttttttt | 420 |
| cggttctctg cttcgcgcca ccgcagcgaa gaagcagagg aacgtacaga tggtgggtcc | 480 |
| gcagaacctg cccaagcaag ggaacacgaa caacaaccgt agtttccagc ctagcggtag | 540 |
| cggcaggcca aggagtagcg gcaacgtcaa tagcaacggg aactggtcaa gatgaaaggc | 600 |
| cccgattcca attccggttc caattctttc aagagcggca gggtcccttt ttttcctttt | 660 |
| tccttttttac atcgg | 675 |

<210> SEQ ID NO 10
<211> LENGTH: 647
<212> TYPE: DNA
<213> ORGANISM: Artificial
<220> FEATURE:
<223> OTHER INFORMATION: PHM1868 reference sequence

<400> SEQUENCE: 10

| | | |
|---|---|---|
| acgttcccgc tgcagaaaga gatgatggca ttccttgcca acacagagaa gcacaaggac | 60 |
| attgaggcct gcgacgaggt gatatctgct tcgatcaaga agatccatga gcatcgcagg | 120 |
| aggagggcct ttttcctggg tttcagccag tccccagtgg agttcatcaa tgctctgata | 180 |
| gcttctcaga gcaaagattt aaagctggtt gctggcgagg cgaataggaa cattgagaaa | 240 |
| gaaagacgtg ccgacttcta taaccaacca tggtattgct cttaggatc aagctgatca | 300 |
| ttgtttttc ttagttgagc attatattat atgtattcat gtgctgatgg gatcacttct | 360 |

```
gtgccataat taaatagggt tgaagacgcc gttataagat acttgaaccg caaaccggct      420
aacgagggcc taggtggtgg tgctggtggt tcttgaggcg tggatttctc ctagctattt      480
tagtgtataa acaaattatc tgttctgtat tggcagtaaa tttcaggcgt attagtgaag      540
ataattgttc agtgttgtga atgatgttc aggctagtca ttgtatgttt atgttgtgtt       600
ctatattgtc aagtgctgaa ctgaaccgta atgtgcttgt ggccaca                    647
```

<210> SEQ ID NO 11
<211> LENGTH: 555
<212> TYPE: DNA
<213> ORGANISM: Artificial
<220> FEATURE:
<223> OTHER INFORMATION: PHM9218 reference sequence

<400> SEQUENCE: 11

```
cgcgcttccc ttagacattc agggagatgc ttcgtatcaa acggacagtg gctgctagcc       60
gtagtcaggt atgccacact tatcaactta gtttacagtt tgacattgac attaacgctt      120
gtatcgcaaa ttaacactga cttgtaatgt tgtgcagaca catttcatac taccggagta      180
cttgatgcag aaggatcaga ggttaaacct ggacgaagca gttgacactc tgaaacgtgc      240
tggcgtccct gaggacgaga tggcagcctt ggaaaggcaa ctggctcccg gaccatccac      300
tgcaccagca gcaacaccaa gcactgcccc agcctctgct aacaggacga tgaacttcgt      360
cagtgctgga gtagaggcgc aggccgagag cagcaggcaa caggctggta acaacgagga      420
cattgagctg cccgatgaga gtgacgacga ggaacccgat gtccaaattg cggagaagag      480
tgttcctgct gcggtatttg gtgagctcgg caagagagct gccgagaata actagtaaaa      540
tgtttttctc ttgtt                                                       555
```

<210> SEQ ID NO 12
<211> LENGTH: 713
<212> TYPE: DNA
<213> ORGANISM: Artificial
<220> FEATURE:
<223> OTHER INFORMATION: PHM505 reference sequence
<220> FEATURE:
<221> NAME/KEY: misc_feature
<222> LOCATION: (2)..(5)
<223> OTHER INFORMATION: n is a, c, g, or t

<400> SEQUENCE: 12

```
tnnnntccat tgcgatcgac ggtagcttct tcatctcctt ctcctgactt gtcacactag       60
gctggcagct ggctgggttc ccgcggatct agtgcgccgc actgcgttct cgccttctgg      120
tgatctggca atgtgcacca gctacgtacg aatcgggtgg acgtggtctc gtggcttgga      180
ctgttgccgg gaattgtttt agcagccgca cgagctcagg ctcttctgtc tgctgctaac      240
cacaagtatg attgatatcc aatgcccaga gtcagctcgg ccgtttgctg caagatctgc      300
acccagagca gaggtgtcgt tgagaatggg aacacagtgt attttatac aggcttgcct       360 tggcctgtct ctctgtctgt cgcacacgat tcactcccaa gtgctcgatc gcgattaatc      420
ctcatggcgt ctaaagatga aaaaaatcta gcgctgttct ggtaggagac tgacggaatt      480
ccccctttcc aggcaatgac gcgcagctcc tcaagggcat caacagctac aggtcctcgc      540
tcaaggtccc ggcgctgtcc gagaacaaga acgcggcgtg cctggccgag cagctcgcaa      600
ggcagttcaa ggggcaggat tcaccaacac gacgggcgcc aaaaccgtca tcggcaccga      660
gcacatttcc ggaatacccca ggtacctgga cccttccact taacgtttgt tac            713
```

<210> SEQ ID NO 13
<211> LENGTH: 519
<212> TYPE: DNA
<213> ORGANISM: Artificial
<220> FEATURE:
<223> OTHER INFORMATION: PHM8340 reference sequence

<400> SEQUENCE: 13

```
ggggacaacc cagtcacgac gcgtcatgaa cgccatcttc agcttcggca acagctgggc      60
cttcgtccac gtaagcacga gcgctcttct ttcgaacgct tattgaggcg tgcttggcac     120
tgacgagcag cgtgtaattc ttcagatcgc ggcgtacggg cgcgggttcg tgcaggcgtc     180
gcggagcacg tggagccagt tcgaggcgct gccggggatg gcggcgctgg tggactcgga     240
catcaccagc tccgtgtgct tcctgacggg cgtgacgagc ggcgcgctgt gcgtggcgct     300
ggcggggtcc tgggcgttcg cgacgcaccg gcactacacg gccaccgtgt cgctgctggc     360
cttctacgtc gggtacctga tgacccgcat cggcatggcg ctgccccagg cgtgcgtcgg     420
ctgctactac gtctgctacg ccgagaaccc cacgtcgcgg ctcttcgacg gtaacatacc     480
gaaccagctg agcaaatgct ggttaatttt ctttatata                            519
```

<210> SEQ ID NO 14
<211> LENGTH: 537
<212> TYPE: DNA
<213> ORGANISM: Artificial
<220> FEATURE:
<223> OTHER INFORMATION: PHM2413 reference sequence
<220> FEATURE:
<221> NAME/KEY: misc_feature
<222> LOCATION: (3)..(5)
<223> OTHER INFORMATION: n is a, c, g, or t

<400> SEQUENCE: 14

```
atnnnatmtc ggtcatcagt aggatcgttg tgggtcacat gactacggca gcatcaaatt      60
tttcggggag acggactgag gtgcctcgat ctggagtcaa ttgtggagtt taacgaccgg     120
gaggttattg tgtacaagga cgatagcaag aagcccctg tgggcgaggg gctgaacaag      180
gctgcagagg tgactctact gaacatcaag tgcgtaaaca agaagaccgg ggagccgtgc     240 caggggcaa gagtggagag gtacagggag atgctggtga agaaggcgga ggagcagggc      300
gcagagtttg tgtccttcga cgctgtcaag ggagattgga agttcagggt gaagcacttc     360
agcgcctacg gctttggtg aaatcctggg gagttaagta gtttgtttgt tctgatggag      420
caacgcttta cgctcttgtc aaataccatg cttggatctg ttgtgctgct tctgtacaat     480
gttgctgctg ttaaaatgct tgcaaattgc acttctatgg tcatagctat ggcttac       537
```

<210> SEQ ID NO 15
<211> LENGTH: 466
<212> TYPE: DNA
<213> ORGANISM: Artificial
<220> FEATURE:
<223> OTHER INFORMATION: PHM12722 reference sequence

<400> SEQUENCE: 15

```
gggaaggtcc cagtcacaac gttgtaagaa agtaccatgg ccaagctctt cgatcaggaa      60
agcttacaat gtaaatggtt gtgggtggcc acagcaagaa gctgcttatg aatgtaaaat     120
caatctcttg acagggaaaa ctcaccaggt atcatgtaac aaacatgcat cactcgaggc     180
ttgatcaata aaaaggttac cgagctaata gcccgccatt atgttgcaga taagggcaca     240
gcttgctgct ataggcgctc ctattatagg ggattctgca tacatgactg cagcaatggc     300
```

```
agcgatggtc aacccaagca taaacccatt cggtagagag aggctgagtt acaacagtga    360
agaggagaaa gaagccgccg tcgaagcatg gattgcctcc cacgggaagg agccaaaatc    420
cgtaattggc tgcaagcgtc agagatctcg ggaaggtgaa aaaata                  466
```

<210> SEQ ID NO 16
<211> LENGTH: 472
<212> TYPE: DNA
<213> ORGANISM: Artificial
<220> FEATURE:
<223> OTHER INFORMATION: PHM9343 reference sequence

<400> SEQUENCE: 16

```
ccaagtcaca ccaagaccaa aaggaaaatt cccagtcaca acagggattg ccaagacgga    60
gtcgccgccg ccgccgccgg agcagcagca gcagcaagaa cagcgtgagc aggcggagca    120
gcagatgcgc gcggagatcg agaggctcaa ggcgcagaac gcggcgctgc agaaggcggc    180
cgaggagagc gcggcggcgc tcagggcgga gctggccggg aaggacgagg agaagcggga    240
ggtgatcagg cagctggcgt cgtccatgga cgtgatgagg caggagaacc tcacgctgcg    300
cgagcacatc agcaggggat cgtcgaagcg ttcctctgcg ccccgcgcgg gagctgcgtt    360
cgatctcagg aaggtggcca ggggcctctt ctccgcgagg ctgttcaccg cgcactgcag    420
gcctacggcc ccatcgtcgc gctctgagca gatgccggac tggtcgttaa at           472
```

<210> SEQ ID NO 17
<211> LENGTH: 607
<212> TYPE: DNA
<213> ORGANISM: Artificial
<220> FEATURE:
<223> OTHER INFORMATION: PHM4462 reference sequence

<400> SEQUENCE: 17

```
ctatcatggt cactacgatg tgtgctttac agccattgta tgtcatggcc ggccaagaat    60
actggccatc ttcgtctcgt agcccatagt gctcaaagct acacaatata cttgacaatg    120
tcaggttagg ccctctccca aattttccat ttctccagtc ttgtatatat gaaggttata    180
gttcttatgc tcaattgatt cttacttgaa gctaaaatgt ggggtgtggg tgcggagcaa    240
ggcggtatcc tacagacatc tactgggaaa cttgaactga aggagccata ctacaggttg    300
tctcagccac aatcctgcac gttgccacaa gatcagcaac agcagcaatt gccatctttg    360
caggcacagg taagatgtaa cttttttctg tagcagcagt tattatttct gaattctgtc    420
tctgaccttc tagaacatgg ttcatcatcc tacacctaac tttgaagcag ttcggctgtt    480
ggcctgctgt ccagtgtaca ttccatgtgc atgcgtagca ggccaacatc cgacctgact    540
accgtgcttc gaagctacac aaggcttttg atagtagtgc ttttcttatt cctacaagtc    600
acttgaa                                                              607
```

<210> SEQ ID NO 18
<211> LENGTH: 654
<212> TYPE: DNA
<213> ORGANISM: Artificial
<220> FEATURE:
<223> OTHER INFORMATION: PHM2109 reference sequence

<400> SEQUENCE: 18

```
tcccaaagga aattttgaag ggggagaagt cagcgaaatt ctggaaaatt cccatcggtt    60
tcttggtgcc ttaagacatt gttataagct aatgtaaaac tgttgagatt ttctatgcta    120
gaagcattga cgtttggctt acattttttt ttgttgccta tttggtttgg tttgatgcaa    180
```

```
tgcaggagag aaccttagct gaagcagaaa ataggccagc cccacctcag tgctgtagcg    240
gcgacgttcg ctccctaaag tttagtgatt tcaagcacgc acatgagcag gtaaaaatgc    300
tacggtcact tgcattattt tgtcttgtaa tctctgttcc tgaatttaat ggccttgtgt    360
ttaggtttgt gcgagtatat catcggattc aaaaaatatg aatgagctcg tccaatggaa    420
cgacctctac ggagaaggcg ggtcgaggca caagacaccg ttgagctact ttatgtagcc    480
taacgttttt ttagatgatt tgtacataca gaagcagcct ttgtataggt gtgtttccag    540
ttaaatttgc tggaaacatt tattcatgtc gggtttcgtt tctataatca actcagcttg    600
tgtctgcatc tagtgtagcc tgagcttctg attagttatt aattattcat ccgt          654
```

<210> SEQ ID NO 19
<211> LENGTH: 551
<212> TYPE: DNA
<213> ORGANISM: Artificial
<220> FEATURE:
<223> OTHER INFORMATION: PHM12598 reference sequence

<400> SEQUENCE: 19

```
agaagcccat caaaacgcta gtggaaagga tatagaggga ccaggagcag atttctgttt     60
cgcagcagtt atttctgcta ctaagcgtag cccacagaac ttttggtatt gtctggttca    120
tgccttctgt cttttcctta ttcctgaaga aatttgtcat attttcttaa atcttgcaca    180
tatggatcag ttaggtttgc tctgcattag aaaaagacta aaaaatttaa cagatcctct    240
ttagccttta aggcgattta gggatcctct gtttctagat tctctttagt tatagaatta    300
tattcaggaa attccttata ctttagtttc ctatcagtgt ctccttgcac tcctttgagc    360
atacaacttt tagtcttcag attttttcat gggtgtcatt ttcttgagaa ttgttgtttg    420
ttttgagtat attattttat cattggccta gaaccttatg acttgtttaa tgcctgcccg    480
ttctttctgt ttctctacca gaggaattgc ttcacatcat ctcaatagaa ctttaagtaa    540
tttcgtatta a                                                         551
```

<210> SEQ ID NO 20
<211> LENGTH: 683
<212> TYPE: DNA
<213> ORGANISM: Artificial
<220> FEATURE:
<223> OTHER INFORMATION: PHM2381 reference sequence

<400> SEQUENCE: 20

```
ggatgtaatc ctaggttgat taaaagccct tatgggggct agggaagagg gggtccttta     60
gtccatgact ggagccaagg ccctgttttt cctccaggtc gaagagttgc tggcttaaaa    120
ctcaaagaag tgggtaatga ccgaagtgt atggaaatac tgatttttt actcatgatg     180 tttctatttt ttatgtaggt tccatgctaa agaataccca gcatttaaca aggaattgtt    240
tccttataat ttgggatatt gccaggcagg taaattttag attattcttt tggtttcctt    300
tcccatcggt gttgtattcg ggtactgtac tttcaagtac ttcattgaat ttattgtcca    360
atccttcttt acaggatcta atgtaccata tgatgattcg atgaatttgc gcaatgtact    420
ttggttagca ccttttgccat caaaggagac aaaagcttgg ttagcaccag gttcggcgat    480
actgaacact caaccatgtt catgtattat aacttgctgt tttcctgata ataaatcagg    540
cctgtgctgt gtatctaatc tgtttccaat ccctatttct acgcgtaaac ttaagtatta    600
tggttaaatc tacaatatgc cacaggagta ctagttgtct tgacgcacat cctgatgaat    660
```

-continued tatctatcaa gagtgtacga caa                                         683

<210> SEQ ID NO 21
<211> LENGTH: 21
<212> TYPE: DNA
<213> ORGANISM: Artificial
<220> FEATURE:
<223> OTHER INFORMATION: PHM1784 forward external primer

<400> SEQUENCE: 21
tcctctgcga atgtgatgat c                                           21

<210> SEQ ID NO 22
<211> LENGTH: 22
<212> TYPE: DNA
<213> ORGANISM: Artificial
<220> FEATURE:
<223> OTHER INFORMATION: PHM1784 forward internal primer

<400> SEQUENCE: 22
taatttggct tgcattctca ct                                          22

<210> SEQ ID NO 23
<211> LENGTH: 19
<212> TYPE: DNA
<213> ORGANISM: Artificial
<220> FEATURE:
<223> OTHER INFORMATION: PHM1784 reverse internal primer

<400> SEQUENCE: 23
ccttgctcct tgtagggag                                              19

<210> SEQ ID NO 24
<211> LENGTH: 20
<212> TYPE: DNA
<213> ORGANISM: Artificial
<220> FEATURE:
<223> OTHER INFORMATION: PHM1784 reverse external primer

<400> SEQUENCE: 24
cgagtctaaa tctgagacac                                             20

<210> SEQ ID NO 25
<211> LENGTH: 21
<212> TYPE: DNA
<213> ORGANISM: Artificial
<220> FEATURE:
<223> OTHER INFORMATION: PHM4743 forward external primer

<400> SEQUENCE: 25
tgtgcagaca aatcatggga c                                           21

<210> SEQ ID NO 26
<211> LENGTH: 21
<212> TYPE: DNA
<213> ORGANISM: Artificial
<220> FEATURE:
<223> OTHER INFORMATION: PHM4743 forward internal primer

<400> SEQUENCE: 26
aaagaccatg agatcctccc t                                           21

<210> SEQ ID NO 27
<211> LENGTH: 20
<212> TYPE: DNA
<213> ORGANISM: Artificial

```
<220> FEATURE:
<223> OTHER INFORMATION: PHM4743 reverse internal primer

<400> SEQUENCE: 27
atggtgtact tctggaggag                                          20

<210> SEQ ID NO 28
<211> LENGTH: 20
<212> TYPE: DNA
<213> ORGANISM: Artificial
<220> FEATURE:
<223> OTHER INFORMATION: PHM4743 reverse external primer

<400> SEQUENCE: 28 tttatccota cgatcgccca                                          20

<210> SEQ ID NO 29
<211> LENGTH: 20
<212> TYPE: DNA
<213> ORGANISM: Artificial
<220> FEATURE:
<223> OTHER INFORMATION: PHM18704 forward external primer

<400> SEQUENCE: 29
gtagccttaa cctgttacat                                          20

<210> SEQ ID NO 30
<211> LENGTH: 21
<212> TYPE: DNA
<213> ORGANISM: Artificial
<220> FEATURE:
<223> OTHER INFORMATION: PHM18704 forward internal primer

<400> SEQUENCE: 30
tcggtaatag ttgtggtggt a                                        21

<210> SEQ ID NO 31
<211> LENGTH: 21
<212> TYPE: DNA
<213> ORGANISM: Artificial
<220> FEATURE:
<223> OTHER INFORMATION: PHM18704 reverse internal primer

<400> SEQUENCE: 31
taagatggga gcaaagatgc t                                        21

<210> SEQ ID NO 32
<211> LENGTH: 18
<212> TYPE: DNA
<213> ORGANISM: Artificial
<220> FEATURE:
<223> OTHER INFORMATION: PHM18704 reverse external primer

<400> SEQUENCE: 32
ggatcagcaa ccagtaag                                            18

<210> SEQ ID NO 33
<211> LENGTH: 21
<212> TYPE: DNA
<213> ORGANISM: Artificial
<220> FEATURE:
<223> OTHER INFORMATION: PHM14460 forward external primer

<400> SEQUENCE: 33
ccttccaaac ccaatctctc a                                        21
```

-continued

<210> SEQ ID NO 34
<211> LENGTH: 19
<212> TYPE: DNA
<213> ORGANISM: Artificial
<220> FEATURE:
<223> OTHER INFORMATION: PHM14460 forward internal primer

<400> SEQUENCE: 34
aagtaccgca actgcgtct                                                    19

<210> SEQ ID NO 35
<211> LENGTH: 20
<212> TYPE: DNA
<213> ORGANISM: Artificial
<220> FEATURE:
<223> OTHER INFORMATION: PHM14460 reverse internal primer

<400> SEQUENCE: 35
acttgagctc ctcaagcgtt                                                   20

<210> SEQ ID NO 36
<211> LENGTH: 21
<212> TYPE: DNA
<213> ORGANISM: Artificial
<220> FEATURE:
<223> OTHER INFORMATION: PHM14460 reverse external primer

<400> SEQUENCE: 36
atcttatcac gggttaagtc c                                                 21

<210> SEQ ID NO 37
<211> LENGTH: 20
<212> TYPE: DNA
<213> ORGANISM: Artificial
<220> FEATURE:
<223> OTHER INFORMATION: PHM11925 forward external primer

<400> SEQUENCE: 37
gtatacggat gctccttgac                                                   20

<210> SEQ ID NO 38
<211> LENGTH: 21
<212> TYPE: DNA
<213> ORGANISM: Artificial
<220> FEATURE:
<223> OTHER INFORMATION: PHM11925 forward internal primer

<400> SEQUENCE: 38
ttgttgggcg tactcattgt t                                                 21

<210> SEQ ID NO 39
<211> LENGTH: 22
<212> TYPE: DNA
<213> ORGANISM: Artificial
<220> FEATURE:
<223> OTHER INFORMATION: PHM11925 reverse internal primer

<400> SEQUENCE: 39
tcagcatgca gttcatgaat tc                                                22

<210> SEQ ID NO 40
<211> LENGTH: 20
<212> TYPE: DNA
<213> ORGANISM: Artificial
<220> FEATURE:
<223> OTHER INFORMATION: PHM11925 reverse external primer

```
<400> SEQUENCE: 40
aatcgctggg ttcattaggt                                            20

<210> SEQ ID NO 41
<211> LENGTH: 22
<212> TYPE: DNA
<213> ORGANISM: Artificial
<220> FEATURE:
<223> OTHER INFORMATION: PHM7853 forward external primer

<400> SEQUENCE: 41
gttgtatatg acagaatgac tg                                         22

<210> SEQ ID NO 42
<211> LENGTH: 21
<212> TYPE: DNA
<213> ORGANISM: Artificial
<220> FEATURE:
<223> OTHER INFORMATION: PHM7853 forward internal primer

<400> SEQUENCE: 42
gtcgagcagt tcaacggtta t                                          21

<210> SEQ ID NO 43
<211> LENGTH: 21
<212> TYPE: DNA
<213> ORGANISM: Artificial
<220> FEATURE:
<223> OTHER INFORMATION: PHM7853 reverse internal primer

<400> SEQUENCE: 43
aaattgacgt ctcggctttg a                                          21

<210> SEQ ID NO 44
<211> LENGTH: 22
<212> TYPE: DNA
<213> ORGANISM: Artificial
<220> FEATURE:
<223> OTHER INFORMATION: PHM7853 reverse external primer

<400> SEQUENCE: 44
tgaaacacac tatcagcctc ta                                         22

<210> SEQ ID NO 45
<211> LENGTH: 22
<212> TYPE: DNA
<213> ORGANISM: Artificial
<220> FEATURE:
<223> OTHER INFORMATION: PHM18903 forward external primer

<400> SEQUENCE: 45
ctatcaccat catccctaga at                                         22

<210> SEQ ID NO 46
<211> LENGTH: 21
<212> TYPE: DNA
<213> ORGANISM: Artificial
<220> FEATURE:
<223> OTHER INFORMATION: PHM18903 forward internal primer

<400> SEQUENCE: 46
tccttcgtct ctcagggtaa t                                          21

<210> SEQ ID NO 47
```

```
<211> LENGTH: 22
<212> TYPE: DNA
<213> ORGANISM: Artificial
<220> FEATURE:
<223> OTHER INFORMATION: PHM18903 reverse internal primer

<400> SEQUENCE: 47
gccatcgatt aaatctcaat aa                                              22

<210> SEQ ID NO 48
<211> LENGTH: 19
<212> TYPE: DNA
<213> ORGANISM: Artificial
<220> FEATURE:
<223> OTHER INFORMATION: PHM18903 reverse external primer

<400> SEQUENCE: 48
tggaggccga tctgttagt                                                  19

<210> SEQ ID NO 49
<211> LENGTH: 22
<212> TYPE: DNA
<213> ORGANISM: Artificial
<220> FEATURE:
<223> OTHER INFORMATION: PHM4828 forward external primer

<400> SEQUENCE: 49
tggtgatatg cgtaggattt ga                                              22

<210> SEQ ID NO 50
<211> LENGTH: 22
<212> TYPE: DNA
<213> ORGANISM: Artificial
<220> FEATURE:
<223> OTHER INFORMATION: PHM4828 forward internal primer

<400> SEQUENCE: 50
gtgaaacatc atatcatgag ga                                              22

<210> SEQ ID NO 51
<211> LENGTH: 22
<212> TYPE: DNA
<213> ORGANISM: Artificial
<220> FEATURE:
<223> OTHER INFORMATION: PHM4828 reverse internal primer

<400> SEQUENCE: 51
cttctgattc tagcttacaa ct                                              22

<210> SEQ ID NO 52
<211> LENGTH: 22
<212> TYPE: DNA
<213> ORGANISM: Artificial
<220> FEATURE:
<223> OTHER INFORMATION: PHM4828 reverse external primer

<400> SEQUENCE: 52
aacgcctacg gaaatatcaa ca                                              22

<210> SEQ ID NO 53
<211> LENGTH: 20
<212> TYPE: DNA
<213> ORGANISM: Artificial
<220> FEATURE:
<223> OTHER INFORMATION: PHM10887 forward external primer

<400> SEQUENCE: 53
```

-continued cagacaaagg agcagttcgt                                               20

<210> SEQ ID NO 54
<211> LENGTH: 18
<212> TYPE: DNA
<213> ORGANISM: Artificial
<220> FEATURE:
<223> OTHER INFORMATION: PHM10887 forward internal primer

<400> SEQUENCE: 54
taggcagcag caccagga                                                 18

<210> SEQ ID NO 55
<211> LENGTH: 21
<212> TYPE: DNA
<213> ORGANISM: Artificial
<220> FEATURE:
<223> OTHER INFORMATION: PHM10887 reverse internal primer

<400> SEQUENCE: 55
aaattgttgt agccgatgta a                                             21

<210> SEQ ID NO 56
<211> LENGTH: 21
<212> TYPE: DNA
<213> ORGANISM: Artificial
<220> FEATURE:
<223> OTHER INFORMATION: PHM10887 reverse external primer

<400> SEQUENCE: 56
tgctgtttat gtactactgg c                                             21

<210> SEQ ID NO 57
<211> LENGTH: 19
<212> TYPE: DNA
<213> ORGANISM: Artificial
<220> FEATURE:
<223> OTHER INFORMATION: PHM1868 forward external primer

<400> SEQUENCE: 57
gctatgatgt gctggtgga                                                19

<210> SEQ ID NO 58
<211> LENGTH: 20
<212> TYPE: DNA
<213> ORGANISM: Artificial
<220> FEATURE:
<223> OTHER INFORMATION: PHM1868 forward internal primer

<400> SEQUENCE: 58
ttcccgctgc agaaagagat                                               20

<210> SEQ ID NO 59
<211> LENGTH: 19
<212> TYPE: DNA
<213> ORGANISM: Artificial
<220> FEATURE:
<223> OTHER INFORMATION: PHM1868 reverse internal primer

<400> SEQUENCE: 59
ttcagggcca caccaagca                                                19

<210> SEQ ID NO 60
<211> LENGTH: 22
<212> TYPE: DNA

```
<213> ORGANISM: Artificial
<220> FEATURE:
<223> OTHER INFORMATION: PHM1868 reverse external primer

<400> SEQUENCE: 60
tagaatgtga tttaggctta ct                                              22

<210> SEQ ID NO 61
<211> LENGTH: 22
<212> TYPE: DNA
<213> ORGANISM: Artificial
<220> FEATURE:
<223> OTHER INFORMATION: PHM9218 forward external primer

<400> SEQUENCE: 61
tttggaagaa gtggaatgac tt                                              22

<210> SEQ ID NO 62
<211> LENGTH: 21
<212> TYPE: DNA
<213> ORGANISM: Artificial
<220> FEATURE:
<223> OTHER INFORMATION: PHM9218 forward internal primer

<400> SEQUENCE: 62
cgaagacaca ttcagggaga t                                               21

<210> SEQ ID NO 63
<211> LENGTH: 20
<212> TYPE: DNA
<213> ORGANISM: Artificial
<220> FEATURE:
<223> OTHER INFORMATION: PHM9218 reverse internal primer

<400> SEQUENCE: 63
tttcctcgtt cttctcggca                                                 20

<210> SEQ ID NO 64
<211> LENGTH: 20
<212> TYPE: DNA
<213> ORGANISM: Artificial
<220> FEATURE:
<223> OTHER INFORMATION: PHM9218 reverse external primer

<400> SEQUENCE: 64
aacggcttac tattggcgtc                                                 20

<210> SEQ ID NO 65
<211> LENGTH: 21
<212> TYPE: DNA
<213> ORGANISM: Artificial
<220> FEATURE:
<223> OTHER INFORMATION: PHM505 forward external primer

<400> SEQUENCE: 65
tgatctacga agaggatgaa t                                               21

<210> SEQ ID NO 66
<211> LENGTH: 18
<212> TYPE: DNA
<213> ORGANISM: Artificial
<220> FEATURE:
<223> OTHER INFORMATION: PHM505 forward internal primer

<400> SEQUENCE: 66
actgcgccag atccgacg                                                   18
```

-continued

<210> SEQ ID NO 67
<211> LENGTH: 21
<212> TYPE: DNA
<213> ORGANISM: Artificial
<220> FEATURE:
<223> OTHER INFORMATION: PHM505 reverse internal primer

<400> SEQUENCE: 67
ataagccacg aagatgttgg t                                              21

<210> SEQ ID NO 68
<211> LENGTH: 20
<212> TYPE: DNA
<213> ORGANISM: Artificial
<220> FEATURE:
<223> OTHER INFORMATION: PHM505 reverse external primer

<400> SEQUENCE: 68
cgagacctga acgtgacaac                                                20

<210> SEQ ID NO 69
<211> LENGTH: 19
<212> TYPE: DNA
<213> ORGANISM: Artificial
<220> FEATURE:
<223> OTHER INFORMATION: PHM8340 forward external primer

<400> SEQUENCE: 69
gagttcatgt tctcctgcg                                                 19

<210> SEQ ID NO 70
<211> LENGTH: 20
<212> TYPE: DNA
<213> ORGANISM: Artificial
<220> FEATURE:
<223> OTHER INFORMATION: PHM8340 forward internal primer

<400> SEQUENCE: 70
cgtcatgaac gccatcttca                                                20

<210> SEQ ID NO 71
<211> LENGTH: 20
<212> TYPE: DNA
<213> ORGANISM: Artificial
<220> FEATURE:
<223> OTHER INFORMATION: PHM8340 reverse internal primer

<400> SEQUENCE: 71
gctttcctgc atcttgctca                                                20

<210> SEQ ID NO 72
<211> LENGTH: 20
<212> TYPE: DNA
<213> ORGANISM: Artificial
<220> FEATURE:
<223> OTHER INFORMATION: PHM8340 reverse external primer

<400> SEQUENCE: 72
aaagaagctc cgtcgtctca                                                20

<210> SEQ ID NO 73
<211> LENGTH: 21
<212> TYPE: DNA
<213> ORGANISM: Artificial
<220> FEATURE:

```
<223> OTHER INFORMATION: PHM2413 forward external primer

<400> SEQUENCE: 73
acgtgcagat tacttcacag a                                              21

<210> SEQ ID NO 74
<211> LENGTH: 19
<212> TYPE: DNA
<213> ORGANISM: Artificial
<220> FEATURE:
<223> OTHER INFORMATION: PHM2413 forward internal primer

<400> SEQUENCE: 74
tcgagtgagg gacttcgtt                                                 19

<210> SEQ ID NO 75
<211> LENGTH: 22
<212> TYPE: DNA
<213> ORGANISM: Artificial
<220> FEATURE:
<223> OTHER INFORMATION: PHM2413 reverse internal primer

<400> SEQUENCE: 75
agcagtgcaa tttgcaagca tt                                             22

<210> SEQ ID NO 76
<211> LENGTH: 19
<212> TYPE: DNA
<213> ORGANISM: Artificial
<220> FEATURE:
<223> OTHER INFORMATION: PHM2413 reverse external primer

<400> SEQUENCE: 76
ggtagcacgc cctcctgtt                                                 19

<210> SEQ ID NO 77
<211> LENGTH: 22
<212> TYPE: DNA
<213> ORGANISM: Artificial
<220> FEATURE:
<223> OTHER INFORMATION: PHM12722 forward external primer

<400> SEQUENCE: 77
ctgtattgaa agatggcatc tc                                             22

<210> SEQ ID NO 78
<211> LENGTH: 20
<212> TYPE: DNA
<213> ORGANISM: Artificial
<220> FEATURE:
<223> OTHER INFORMATION: PHM12722 forward internal primer

<400> SEQUENCE: 78
ttgtaggaag gtaccatggc                                                20

<210> SEQ ID NO 79
<211> LENGTH: 20
<212> TYPE: DNA
<213> ORGANISM: Artificial
<220> FEATURE:
<223> OTHER INFORMATION: PHM12722 reverse internal primer

<400> SEQUENCE: 79
gatcccaaga gatctctgac                                                20
```

```
<210> SEQ ID NO 80
<211> LENGTH: 20
<212> TYPE: DNA
<213> ORGANISM: Artificial
<220> FEATURE:
<223> OTHER INFORMATION: PHM12722 reverse external primer

<400> SEQUENCE: 80
cagccttgta agaatggtgc                                                 20

<210> SEQ ID NO 81
<211> LENGTH: 20
<212> TYPE: DNA
<213> ORGANISM: Artificial
<220> FEATURE:
<223> OTHER INFORMATION: PHM9343 forward external primer

<400> SEQUENCE: 81
caggaagaat acgaggcaga                                                 20

<210> SEQ ID NO 82
<211> LENGTH: 19
<212> TYPE: DNA
<213> ORGANISM: Artificial
<220> FEATURE:
<223> OTHER INFORMATION: PHM9343 forward internal primer

<400> SEQUENCE: 82
gggatggcca agacggagt                                                  19

<210> SEQ ID NO 83
<211> LENGTH: 21
<212> TYPE: DNA
<213> ORGANISM: Artificial
<220> FEATURE:
<223> OTHER INFORMATION: PHM9343 reverse internal primer

<400> SEQUENCE: 83
atcctggcat cctgctcaga g                                               21

<210> SEQ ID NO 84
<211> LENGTH: 21
<212> TYPE: DNA
<213> ORGANISM: Artificial
<220> FEATURE:
<223> OTHER INFORMATION: PHM9343 reverse external primer

<400> SEQUENCE: 84
gcatatctac gctgtctctc t                                               21

<210> SEQ ID NO 85
<211> LENGTH: 20
<212> TYPE: DNA
<213> ORGANISM: Artificial
<220> FEATURE:
<223> OTHER INFORMATION: PHM4462 forward external primer

<400> SEQUENCE: 85
aaaggtggct taccactgct                                                 20

<210> SEQ ID NO 86
<211> LENGTH: 21
<212> TYPE: DNA
<213> ORGANISM: Artificial
<220> FEATURE:
<223> OTHER INFORMATION: PHM4462 forward internal primer
```

```
<400> SEQUENCE: 86
tacaactcac tggtaccaac t                                          21

<210> SEQ ID NO 87
<211> LENGTH: 20
<212> TYPE: DNA
<213> ORGANISM: Artificial
<220> FEATURE:
<223> OTHER INFORMATION: PHM4462 reverse internal primer

<400> SEQUENCE: 87
ttagcctttg gcagctaacg                                            20

<210> SEQ ID NO 88
<211> LENGTH: 20
<212> TYPE: DNA
<213> ORGANISM: Artificial
<220> FEATURE:
<223> OTHER INFORMATION: PHM4462 reverse external primer

<400> SEQUENCE: 88
ggtacacctc gatcgtgata                                            20

<210> SEQ ID NO 89
<211> LENGTH: 20
<212> TYPE: DNA
<213> ORGANISM: Artificial
<220> FEATURE:
<223> OTHER INFORMATION: PHM2109 forward external primer

<400> SEQUENCE: 89
cagatgggta ttcaggcagt                                            20

<210> SEQ ID NO 90
<211> LENGTH: 19
<212> TYPE: DNA
<213> ORGANISM: Artificial
<220> FEATURE:
<223> OTHER INFORMATION: PHM2109 forward internal primer

<400> SEQUENCE: 90
ctgcagcaca tcgtcccat                                             19

<210> SEQ ID NO 91
<211> LENGTH: 22
<212> TYPE: DNA
<213> ORGANISM: Artificial
<220> FEATURE:
<223> OTHER INFORMATION: PHM2109 reverse internal primer

<400> SEQUENCE: 91
gatccaacgg actgaaataa at                                         22

<210> SEQ ID NO 92
<211> LENGTH: 20
<212> TYPE: DNA
<213> ORGANISM: Artificial
<220> FEATURE:
<223> OTHER INFORMATION: PHM2109 reverse external primer

<400> SEQUENCE: 92
atctccgtcg agacctttca                                            20

<210> SEQ ID NO 93
<211> LENGTH: 22
```

```
<210> SEQ ID NO 93
<211> LENGTH: 22
<212> TYPE: DNA
<213> ORGANISM: Artificial
<220> FEATURE:
<223> OTHER INFORMATION: PHM12598 forward external primer

<400> SEQUENCE: 93
taatacaggt gtgctttaga tg                                              22

<210> SEQ ID NO 94
<211> LENGTH: 21
<212> TYPE: DNA
<213> ORGANISM: Artificial
<220> FEATURE:
<223> OTHER INFORMATION: PHM12598 forward internal primer

<400> SEQUENCE: 94
ctagtggaaa ggatatagag g                                               21

<210> SEQ ID NO 95
<211> LENGTH: 22
<212> TYPE: DNA
<213> ORGANISM: Artificial
<220> FEATURE:
<223> OTHER INFORMATION: PHM12598 reverse internal primer

<400> SEQUENCE: 95
cacacttaac agttctattg ag                                              22

<210> SEQ ID NO 96
<211> LENGTH: 22
<212> TYPE: DNA
<213> ORGANISM: Artificial
<220> FEATURE:
<223> OTHER INFORMATION: PHM12598 reverse external primer

<400> SEQUENCE: 96
cttcatcaga ggctaaatga tt                                              22

<210> SEQ ID NO 97
<211> LENGTH: 19
<212> TYPE: DNA
<213> ORGANISM: Artificial
<220> FEATURE:
<223> OTHER INFORMATION: PHM2381 forward external primer

<400> SEQUENCE: 97
atcggagaca ggacggctt                                                  19

<210> SEQ ID NO 98
<211> LENGTH: 22
<212> TYPE: DNA
<213> ORGANISM: Artificial
<220> FEATURE:
<223> OTHER INFORMATION: PHM2381 forward internal primer

<400> SEQUENCE: 98
caaataccat acaacactct ga                                              22

<210> SEQ ID NO 99
<211> LENGTH: 22
<212> TYPE: DNA
<213> ORGANISM: Artificial
<220> FEATURE:
<223> OTHER INFORMATION: PHM2381 reverse internal primer

<400> SEQUENCE: 99
```

```
tagtcacgta tcatctcttg at                                              22

<210> SEQ ID NO 100
<211> LENGTH: 20
<212> TYPE: DNA
<213> ORGANISM: Artificial
<220> FEATURE:
<223> OTHER INFORMATION: PHM2381 reverse external primer

<400> SEQUENCE: 100
atctacggga gctgcatttg                                                 20

<210> SEQ ID NO 101
<211> LENGTH: 17
<212> TYPE: DNA
<213> ORGANISM: artificial
<220> FEATURE:
<223> OTHER INFORMATION: PHM4743-50-A forward primer

<400> SEQUENCE: 101
cggcatcgct gggygca                                                    17

<210> SEQ ID NO 102
<211> LENGTH: 17
<212> TYPE: DNA
<213> ORGANISM: artificial
<220> FEATURE:
<223> OTHER INFORMATION: PHM18903-29-A forward primer

<400> SEQUENCE: 102
gcgactggac aacggcc                                                    17

<210> SEQ ID NO 103
<211> LENGTH: 19
<212> TYPE: DNA
<213> ORGANISM: artificial
<220> FEATURE:
<223> OTHER INFORMATION: PHM8340-5-A forward primer

<400> SEQUENCE: 103
gcacgtggag ccagttcga                                                  19

<210> SEQ ID NO 104
<211> LENGTH: 18
<212> TYPE: DNA
<213> ORGANISM: artificial
<220> FEATURE:
<223> OTHER INFORMATION: PHM9343-12-A forward primer

<400> SEQUENCE: 104
gcgggaggtg atcaggca                                                   18

<210> SEQ ID NO 105
<211> LENGTH: 18
<212> TYPE: DNA
<213> ORGANISM: artificial
<220> FEATURE:
<223> OTHER INFORMATION: PHM4743-50-A reverse primer

<400> SEQUENCE: 105
gccctggtac aggcacga                                                   18

<210> SEQ ID NO 106
<211> LENGTH: 30
<212> TYPE: DNA
<213> ORGANISM: artificial
```

```
<220> FEATURE:
<223> OTHER INFORMATION: PHM18903-29-A reverse primer

<400> SEQUENCE: 106
agggaattaa cwggcatgct ggatttcaga                                      30

<210> SEQ ID NO 107
<211> LENGTH: 17
<212> TYPE: DNA
<213> ORGANISM: artificial
<220> FEATURE:
<223> OTHER INFORMATION: PHM8340-5-A reverse primer

<400> SEQUENCE: 107
cgcccgtcag gaagcac                                                    17

<210> SEQ ID NO 108
<211> LENGTH: 18
<212> TYPE: DNA
<213> ORGANISM: artificial
<220> FEATURE:
<223> OTHER INFORMATION: PHM9343-12-A reverse primer

<400> SEQUENCE: 108
ccctggccac cttcctga                                                   18

<210> SEQ ID NO 109
<211> LENGTH: 13
<212> TYPE: DNA
<213> ORGANISM: artificial
<220> FEATURE:
<223> OTHER INFORMATION: PHM4743-50-A probe 1

<400> SEQUENCE: 109
tagccacccg tgg                                                        13

<210> SEQ ID NO 110
<211> LENGTH: 16
<212> TYPE: DNA
<213> ORGANISM: artificial
<220> FEATURE:
<223> OTHER INFORMATION: PHM18903-29-A probe 1

<400> SEQUENCE: 110
tgacgacggg aatcta                                                     16

<210> SEQ ID NO 111
<211> LENGTH: 12
<212> TYPE: DNA
<213> ORGANISM: artificial
<220> FEATURE:
<223> OTHER INFORMATION: PHM8340-5-A probe 1

<400> SEQUENCE: 111
acgccgccat cc                                                         12

<210> SEQ ID NO 112
<211> LENGTH: 15
<212> TYPE: DNA
<213> ORGANISM: artificial
<220> FEATURE:
<223> OTHER INFORMATION: PHM9343-12-A probe 1

<400> SEQUENCE: 112
gtcccctgct gatgt                                                      15
```

<210> SEQ ID NO 113
<211> LENGTH: 13
<212> TYPE: DNA
<213> ORGANISM: artificial
<220> FEATURE:
<223> OTHER INFORMATION: PHM4743-50-A probe 2

<400> SEQUENCE: 113
cagccacccg tgg                                                        13

<210> SEQ ID NO 114
<211> LENGTH: 15
<212> TYPE: DNA
<213> ORGANISM: artificial
<220> FEATURE:
<223> OTHER INFORMATION: PHM18903-29-A probe 2

<400> SEQUENCE: 114
cgacgacggg aatct                                                      15

<210> SEQ ID NO 115
<211> LENGTH: 11
<212> TYPE: DNA
<213> ORGANISM: artificial
<220> FEATURE:
<223> OTHER INFORMATION: PHM8340-5-A probe 2

<400> SEQUENCE: 115
gcgccgccat c                                                          11

<210> SEQ ID NO 116
<211> LENGTH: 15
<212> TYPE: DNA
<213> ORGANISM: artificial
<220> FEATURE:
<223> OTHER INFORMATION: PHM9343-12-A probe 2

<400> SEQUENCE: 116
atcccctgct gatgt                                                      15

<210> SEQ ID NO 117
<211> LENGTH: 22
<212> TYPE: DNA
<213> ORGANISM: artificial
<220> FEATURE:
<223> OTHER INFORMATION: PHM505-250-A forward primer

<400> SEQUENCE: 117
gctacgtacg aatcgggtgg ac                                              22

<210> SEQ ID NO 118
<211> LENGTH: 30
<212> TYPE: DNA
<213> ORGANISM: artificial
<220> FEATURE:
<223> OTHER INFORMATION: PHM2413-17-B forward primer

<400> SEQUENCE: 118
tctactgaac atcaagtgcg taaacaagaa                                      30

<210> SEQ ID NO 119
<211> LENGTH: 34

```
<212> TYPE: DNA
<213> ORGANISM: artificial
<220> FEATURE:
<223> OTHER INFORMATION: PHM4828-12-U forward primer

<400> SEQUENCE: 119
cgaatttgaa ctggttccca atattttgtt ctcc                              34

<210> SEQ ID NO 120
<211> LENGTH: 20
<212> TYPE: DNA
<213> ORGANISM: artificial
<220> FEATURE:
<223> OTHER INFORMATION: PHM9218-16-U forward primer

<400> SEQUENCE: 120
tgaggacgag atggcagcct                                              20

<210> SEQ ID NO 121
<211> LENGTH: 20
<212> TYPE: DNA
<213> ORGANISM: artificial
<220> FEATURE:
<223> OTHER INFORMATION: PHM505-250-A reverse primer

<400> SEQUENCE: 121
caacgacacc tctgctctgg                                              20

<210> SEQ ID NO 122
<211> LENGTH: 22
<212> TYPE: DNA
<213> ORGANISM: artificial
<220> FEATURE:
<223> OTHER INFORMATION: PHM2413-17-B reverse primer

<400> SEQUENCE: 122
ccccaggatt tcaccaaagc cc                                           22

<210> SEQ ID NO 123
<211> LENGTH: 24
<212> TYPE: DNA
<213> ORGANISM: artificial
<220> FEATURE:
<223> OTHER INFORMATION: PHM4828-12-U reverse primer

<400> SEQUENCE: 123
tcgcctttga tggatcgtgc aaag                                         24

<210> SEQ ID NO 124
<211> LENGTH: 22
<212> TYPE: DNA
<213> ORGANISM: artificial
<220> FEATURE:
<223> OTHER INFORMATION: PHM9218-16-U reverse primer

<400> SEQUENCE: 124
cgtcctgtta gcagaggctg gg                                           22

<210> SEQ ID NO 125
<211> LENGTH: 19
<212> TYPE: DNA
<213> ORGANISM: artificial
<220> FEATURE:
<223> OTHER INFORMATION: PHM505-250-A probe 1

<400> SEQUENCE: 125
```

```
cgctaaccac aagtatgat                                                  19

<210> SEQ ID NO 126
<211> LENGTH: 16
<212> TYPE: DNA
<213> ORGANISM: artificial
<220> FEATURE:
<223> OTHER INFORMATION: PHM2413-17-B probe 1

<400> SEQUENCE: 126
atctcccttg acagcg                                                     16

<210> SEQ ID NO 127
<211> LENGTH: 32
<212> TYPE: DNA
<213> ORGANISM: artificial
<220> FEATURE:
<223> OTHER INFORMATION: PHM4828-12-U probe 1

<400> SEQUENCE: 127
cgcgccgagg cccgttaatt gctaacttaa aa                                   32

<210> SEQ ID NO 128
<211> LENGTH: 25
<212> TYPE: DNA
<213> ORGANISM: artificial
<220> FEATURE:
<223> OTHER INFORMATION: PHM9218-16-U probe 1

<400> SEQUENCE: 128
cgcgccgagg tggaccatcc actgc                                           25

<210> SEQ ID NO 129
<211> LENGTH: 20
<212> TYPE: DNA
<213> ORGANISM: artificial
<220> FEATURE:
<223> OTHER INFORMATION: PHM505-250-A probe 2

<400> SEQUENCE: 129
tgctaaccac aagtatgatt                                                 20

<210> SEQ ID NO 130
<211> LENGTH: 15
<212> TYPE: DNA
<213> ORGANISM: artificial
<220> FEATURE:
<223> OTHER INFORMATION: PHM2413-17-B probe 2

<400> SEQUENCE: 130
ctctcccttg acagc                                                      15

<210> SEQ ID NO 131
<211> LENGTH: 33
<212> TYPE: DNA
<213> ORGANISM: artificial
<220> FEATURE:
<223> OTHER INFORMATION: PHM4828-12-U probe 2

<400> SEQUENCE: 131
acggacgcgg aggccgttaa ttgctaactt aaa                                  33

<210> SEQ ID NO 132
<211> LENGTH: 26
<212> TYPE: DNA
<213> ORGANISM: artificial
```

```
<220> FEATURE:
<223> OTHER INFORMATION: PHM9218-16-U probe 2

<400> SEQUENCE: 132
acggacgcgg agcggaccat ccactg                                              26
```

GENETIC LOCI ASSOCIATED WITH NORTHERN LEAF BLIGHT RESISTANCE IN MAIZE

CROSS-REFERENCE TO RELATED APPLICATION

This application claims the benefit of U.S. Provisional Application No. 61/104,804, filed Oct. 13, 2008, which is incorporated by reference in its entirety.

FIELD OF THE INVENTION

The present disclosure relates to compositions and methods useful in enhancing resistance to northern leaf blight in maize plants.

BACKGROUND OF THE INVENTION

Northern leaf blight (NLB), induced by the fungal pathogen *Exserohilum turcicum* (previously called *Helminthosporium turcicum*), is a serious foliar wilt disease of maize in many tropical and temperate environments. Symptoms can range from cigar-shaped lesions on the lower leaves to complete destruction of the foliage, thereby reducing the amount of leaf surface area available for photosynthesis. A reduction in photosynthetic capability leads to a lack of carbohydrates needed for grain fill, which impacts grain yield. Mid-altitude regions of the tropics, about 900-1600 m above sea level, have a particularly favorable climate for northern leaf blight, as dew periods are long and temperatures moderate. However, northern leaf blight can also yield losses of 30-50% in temperate environments, such as in the United States, during wet seasons, particularly if the infection is established on the upper leaves of the plant by the silking stage.

The fungus *Exserohilum turcicum* (Et) overwinters as mycelia and conidia on maize residues left on the soil surface. The conidia are transformed into resting spores, and during warm, moist weather, new conidia are produced and then carried by wind or rain to lower leaves of young maize plants. Infection requires the presence of water on the leaf surface for 6-18 hours and a temperature of between 66 and 80° F. If infection occurs, lesions develop within 7-12 days and produce new conidia, which spread the infection to secondary sites. Disease management strategies include crop rotation, destruction of old maize residues by tillage, and fungicide application, all of which are aimed at reducing the fungal inoculum. However, the most effective and most preferred method of control for northern leaf blight is the planting of resistant hybrids.

Several varieties or races of *Exserohilum turcicum* are present in nature, leaving growers with two hybrid options: partial resistant hybrids, which offer low-level, broad spectrum protection against multiple races, and race-specific resistant hybrids, which protect against a specific race. Genetic sources of resistance to *Exserohilum turcicum* have been described, and four *Exserohilum turcicum* (previously called *Helminthosporium turcicum*) resistance loci have been identified: Ht1, Ht2, Ht3, and Htn1. Gene Ht1 maps to the long arm of chromosome 2 where it is closely linked to umc36 (Coe, E. H. et al. (1988), *Corn and Corn Improvement,* 3rd *edn*., pp. 81-258), sgcr506 (Gupta, M. et al. (1989) *Maize Genet. Coop. Newsl.* 63, 112), umc150B (Bentolila, S. et al. (1991) *Theor. Appl. Genet.,* 82:393-398), and pic18a (Collins et al. (1998) *Molecular Plant-Microbe Interactions,* 11:968-978), and it is closely flanked by umc22 and umc122 (Li et al. (1998) *Hereditas,* 129:101-106). Gene Ht2 maps to the long arm of chromosome 8 in the umc48-umc89 interval (Zaitlin et al. (1992) *Maize Genet. Coop. Newsl.,* 66, 69-70), and gene Ht3 maps to chromosome 7 near bnlg1666 (Van Staden, D et al. (2001) *Maize Genetics Conference Abstracts* 43:P134). The Htn1 gene maps to chromosome 8, approximately 10 cM distal to Ht2 and 0.8 cM distal to the RFLP marker umc117 (Simcox and Bennetzen (1993) *Maize Genet. Coop. Newl.* 67, 118-119; Simcox and Bennetzen (1993) *Phytopathology,* 83:1326-1330).

The methods of controlling northern leaf blight by reducing fungal inoculum require additional time and resources on the part of the farmer, and in addition, can have detrimental effects on the environment. This makes the planting of resistant hybrids even more attractive to farmers and the general public. Thus, it is desirable to provide compositions and methods for identifying and selecting maize plants with enhanced resistance to northern leaf blight. These plants can be used in breeding programs to generate high-yielding hybrids with resistance to *Exserohilum* and/or northern leaf blight.

SUMMARY

Compositions and methods for identifying and selecting maize plants with enhanced resistance to *Exserohilum* and/or northern leaf blight are provided.

In one embodiment, methods of selecting a maize plant or germplasm with enhanced resistance to *Exserohilum* and/or northern leaf blight are provided. In these methods, DNA is obtained, and the presence of at least one marker allele is detected. The marker allele can include any marker allele that is linked to and associated with: a haplotype comprising a "G" at PHM4743.50, a "G" at PHM18903.29, a "T" at PHM505.250, a "C" at PHM8340.5, a "G" at PHM2413.17, and a "C" at PHM9343.12; a haplotype comprising an "A" at PHM4743.50, an "A" at PHM18903.29, a "T" at PHM505.250, a "T" at PHM8340.5, a "T" at PHM2413.17, and a "T" at PHM9343.12; an "A" at PHM18903.29, a "T" at PHM9218.16, and a "C" at PHM4828.12; or a "C" at PHM4828.12. A maize plant or germplasm that has a marker allele linked to and associated with any of these haplotypes or marker alleles can then be selected. Maize plants identified by this method are also of interest. Progeny and seeds derived from the maize plants selected by this method are also of interest.

In another embodiment, methods for identifying maize plants with enhanced resistance to *Exserohilum* and/or northern leaf blight by detecting a marker locus in the genome of the maize plant using the sequence of the marker locus, a portion of the sequence of the marker locus, or a complement of the sequence of the marker locus, or of a portion thereof, as a marker probe, are provided. The marker probe hybridizes under stringent conditions to the contiguous DNA between and including SEQ ID NO:1, or a nucleotide sequence that is 95% identical to SEQ ID NO:1 based on the Clustal V method of alignment, and SEQ ID NO:20, or a nucleotide sequence that is 95% identical to SEQ ID NO:20 based on the Clustal V method of alignment, and the marker locus comprises at least one allele that is associated with enhanced resistance to *Exserohilum* and/or northern leaf blight. Maize plants identified by this method are also of interest. Progeny and seeds derived from the maize plants selected by this method are also of interest.

In another embodiment, methods for identifying maize plants with enhanced resistance to *Exserohilum* and/or northern leaf blight by detecting at least one marker allele associated with the enhanced resistance in the germplasm of a maize plant are provided. The marker locus can be selected from any of the following marker loci: PHM1784, PHM4743, PHM18704, PHM14460, PHM11925, PHM7853, PHM18903, PHM10887, PHM1868, PHM9218, PHM12722, PHM4828, PHM505, PHM8340, PHM9343, PHM2413, PHM12598, PHM2381, PHM4462, and PHM2109, as well as any other marker that is linked to these markers. The marker locus can also be found within any of the following intervals on chromosome 2, comprising and flanked by:

(i) PHM1784 and PHM2381;
(ii) PHM18704 and PHM2381;
(iii) PHM18704 and PHM8340; and
(iv) PHM10887 and PHM8340.

The marker locus comprises at least one allele that is associated with enhanced resistance to *Exserohilum* and/or northern leaf blight. Maize plants identified by this method are also of interest. Progeny and seeds derived from the maize plants selected by this method are also of interest.

In another embodiment, methods for identifying maize plants with enhanced resistance to *Exserohilum* and/or northern leaf blight by detecting a haplotype in the germplasm of the maize plant are provided. The haplotype comprises alleles at one or more marker loci, wherein the one or more marker loci are found within any of the following intervals on chromosome 2, comprising and flanked by:

(i) PHM1784 and PHM2381;
(ii) PHM18704 and PHM2381;
(iii) PHM18704 and PHM8340; and
(iv) PHM10887 and PHM8340.

The haplotype is associated with enhanced resistance to *Exserohilum* and/or northern leaf blight.

In another embodiment, the haplotype comprises the following alleles: a "G" at PHM4743.50, a "G" at PHM18903.29, a "T" at PHM505.250, a "C" at PHM8340.5, a "G" at PHM2413.17, and a "C" at PHM9343.12.

In another embodiment, the haplotype comprises the following alleles: an "A" at PHM4743.50, an "A" at PHM18903.29, a "T" at PHM505.250, a "T" at PHM8340.5, a "T" at PHM2413.17, and a "T" at PHM9343.12.

In another embodiment, the haplotype comprises the following alleles: an "A" at PHM189036.29, a "C" at PHM4828.12, and a "T" at PHM9218.16.

Maize plants identified by these methods are also of interest. Progeny and seeds derived from the maize plants selected by this method are also of interest.

In another embodiment, methods of selecting maize plants with enhanced resistance to *Exserohilum* and/or northern leaf blight are provided. In one aspect, a first maize plant is obtained that has at least one allele of a marker locus wherein the allele is associated with the enhanced resistance. The marker locus can be found within any of the following intervals on chromosome 2, comprising and flanked by:

(i) PHM1784 and PHM2381;
(ii) PHM18704 and PHM2381;
(iii) PHM18704 and PHM8340; and
(iv) PHM10887 and PHM8340.

The first maize plant can be crossed to a second maize plant, and the progeny resulting from the cross can be evaluated for the allele of the first maize plant. Progeny plants that possess the allele from the first maize plant can be selected as having enhanced resistance to *Exserohilum* and/or northern leaf blight. Maize plants selected by this method are also of interest. Progeny and seeds derived from the maize plants selected by this method are also of interest.

In another embodiment, methods of selecting maize plants with enhanced resistance to *Exserohilum* and/or northern leaf blight are provided. In one aspect, a first maize plant is obtained that has a "G" at PHM4743.50, a "G" at PHM18903.29, a "T" at PHM505.250, a "C" at PHM8340.5, a "G" at PHM2413.17, and a "C" at PHM9343.12. The first maize plant can be crossed to a second maize plant, and the progeny resulting from the cross can be evaluated at PHM4743.50, PHM18903.29, PHM505.250, PHM8340.5, PHM2413.17, and PHM9343.12. Progeny plants that possess a "G" at PHM4743.50, a "G" at PHM18903.29, a "T" at PHM505.250, a "C" at PHM8340.5, a "G" at PHM2413.17, and a "C" at PHM9343.12, can be selected as having enhanced resistance to *Exserohilum* and/or northern leaf blight. Maize plants selected by this method are also of interest. Progeny and seeds derived from the maize plants selected by this method are also of interest.

In another embodiment, methods of selecting maize plants with enhanced resistance to *Exserohilum* and/or northern leaf blight are provided. In one aspect, a first maize plant is obtained that has an "A" at PHM4743.50, an "A" at PHM18903.29, a "T" at PHM505.250, a "T" at PHM8340.5, a "T" at PHM2413.17, and a "T" at PHM9343.12. The first maize plant can be crossed to a second maize plant, and the progeny resulting from the cross can be evaluated at PHM4743.50, PHM18903.29, PHM505.250, PHM8340.5, PHM2413.17, and PHM9343.12. Progeny plants that possess an "A" at PHM4743.50, an "A" at PHM18903.29, a "T" at PHM505.250, a "T" at PHM8340.5, a "T" at PHM2413.17, and a "T" at PHM9343.12, can be selected as having enhanced resistance to *Exserohilum* and/or northern leaf blight. Maize plants selected by this method are also of interest. Progeny and seeds derived from the maize plants selected by this method are also of interest.

In another embodiment, methods of selecting maize plants with enhanced resistance to *Exserohilum* and/or northern leaf blight are provided. In one aspect, a first maize plant is obtained that has an "A" at PHM18903.29, a "C" at PHM4828.12, and a "T" at PHM9218.16. The first maize plant can be crossed to a second maize plant, and the progeny resulting from the cross can be evaluated at PHM18903.29, PHM4828.12, and PHM9218.16. Progeny plants that possess an "A" at PHM18903.29, a "C" at PHM4828.12, and a "T" at PHM9218.16, can be selected as having enhanced resistance to *Exserohilum* and/or northern leaf blight. Maize plants selected by this method are also of interest. Progeny and seeds derived from the maize plants selected by this method are also of interest.

BRIEF DESCRIPTION OF FIGURES AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIGS. 1A and 1B show the physical map arrangement of sequenced BACs (obtained from the Maize Genome Browser, which is publicly available on the internet; http://www.maizesequence.org) that assemble to the region defined by and including PHM1784 (SEQ ID NO:1) and PHM2381 (SEQ ID NO:20). The positions of the PHM markers described herein are indicated, as are the positions of the public markers lying within the interval.

FIG. 2 shows the markers on chromosome 2 that co-segregate with northern leaf blight resistance in the Stiff Stalk subpopulation at a p-level ≤0.001. The lines used in the association analysis had northern leaf blight scores of 1 and 9. Distance expressed in cM on Chr. 2. Y axis: probability value.

FIG. 3 shows the diagram used as a guide to score northern leaf blight infection.

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

TABLE 1

PHM Markers

| Marker Locus | Reference sequence (SEQ ID NO:) | | Primers Forward (SEQ ID NO:) | Reverse (SEQ ID NO:) |
|---|---|---|---|---|
| PHM1784 | 1 | Internal | 22 | 23 |
| | | External | 21 | 24 |
| PHM4743 | 2 | Internal | 26 | 27 |
| | | External | 25 | 28 |
| PHM18704 | 3 | Internal | 30 | 31 |
| | | External | 29 | 32 |
| PHM14460 | 4 | Internal | 34 | 35 |
| | | External | 33 | 36 |
| PHM11925 | 5 | Internal | 38 | 39 |
| | | External | 37 | 40 |
| PHM7853 | 6 | Internal | 42 | 43 |
| | | External | 41 | 44 |
| PHM18903 | 7 | Internal | 46 | 47 |
| | | External | 45 | 48 |
| PHM4828 | 8 | Internal | 50 | 51 |
| | | External | 49 | 52 |
| PHM10887 | 9 | Internal | 54 | 55 |
| | | External | 53 | 56 |
| PHM1868 | 10 | Internal | 58 | 59 |
| | | External | 57 | 60 |
| PHM9218 | 11 | Internal | 62 | 63 |
| | | External | 61 | 64 |
| PHM505 | 12 | Internal | 66 | 67 |
| | | External | 65 | 68 |
| PHM8340 | 13 | Internal | 70 | 71 |
| | | External | 69 | 72 |
| PHM2413 | 14 | Internal | 74 | 75 |
| | | External | 73 | 76 |
| PHM12722 | 15 | Internal | 78 | 79 |
| | | External | 77 | 80 |
| PHM9343 | 16 | Internal | 82 | 83 |
| | | External | 81 | 84 |
| PHM4462 | 17 | Internal | 86 | 87 |
| | | External | 85 | 88 |
| PHM2109 | 18 | Internal | 90 | 91 |
| | | External | 89 | 92 |
| PHM12598 | 19 | Internal | 94 | 95 |
| | | External | 93 | 96 |
| PHM2381 | 20 | Internal | 98 | 99 |
| | | External | 97 | 100 |

TABLE 2

SNP Production Markers

| Production Marker | SNP | Forward primer | Reverse primer | Allele 1 | Allele 2 | Probe 1 | Probe 2 |
|---|---|---|---|---|---|---|---|
| PHM4743-50-A | PHM4743.50 | SEQ ID NO: 101 | SEQ ID NO: 105 | A | G | SEQ ID NO: 109 | SEQ ID NO: 113 |
| PHM18903-29-A | PHM18903.29 | SEQ ID NO: 102 | SEQ ID NO: 106 | A | G | SEQ ID NO: 110 | SEQ ID NO: 114 |
| PHM8340-5-A | PHM8340.5 | SEQ ID NO: 103 | SEQ ID NO: 107 | T | C | SEQ ID NO: 111 | SEQ ID NO: 115 |
| PHM9343-12-A | PHM9343.12 | SEQ ID NO: 104 | SEQ ID NO: 108 | C | T | SEQ ID NO: 112 | SEQ ID NO: 116 |
| PHM505-250-A | PHM505.250 | SEQ ID NO: 117 | SEQ ID NO: 121 | C | T | SEQ ID NO: 125 | SEQ ID NO: 129 |
| PHM2413-17-B | PHM2413.17 | SEQ ID NO: 118 | SEQ ID NO: 122 | T | G | SEQ ID NO: 126 | SEQ ID NO: 130 |
| PHM4828-12-U | PHM4828.12 | SEQ ID NO: 119 | SEQ ID NO: 123 | G | C | SEQ ID NO: 127 | SEQ ID NO: 131 |
| PHM9218-16-U | PHM9218.16 | SEQ ID NO: 120 | SEQ ID NO: 124 | T | C | SEQ ID NO: 128 | SEQ ID NO: 132 |

SEQ ID NOs: 1-100 (See Table 1: PHM Markers).

SEQ ID NOs: 101-132 (See Table 2: SNP Production Markers).

DETAILED DESCRIPTION

The present invention provides allelic compositions in maize and methods for identifying and selecting maize plants with enhanced resistance to *Exserohilum* and/or northern leaf blight. The following definitions are provided as an aid to understand this invention.

The term "allele" refers to one of two or more different nucleotide sequences that occur at a specific locus.

An "amplicon" is an amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. The assemblies can be found using the Maize Genome Browser, which is publicly available on the internet.

An allele is "associated with" a trait when it is linked to it and when the presence of the allele is an indicator that the desired trait or trait form will occur in a plant comprising the allele.

A "BAC", or bacterial artificial chromosome, is a cloning vector derived from the naturally occurring F factor of *Escherichia coli*. BACs can accept large inserts of DNA sequence. In maize, a number of BACs, or bacterial artificial chromosomes, each containing a large insert of maize genomic DNA, have been assembled into contigs (overlapping contiguous genetic fragments, or "contiguous DNA").

"Backcrossing" refers to the process whereby hybrid progeny are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in *Techniques et Utilisations des Marqueurs Moleculaires Les Colloques*, Vol. 72, pp. 45-56, and Openshaw et al., (1994) *Marker-assisted Selection in Backcross Breeding, Analysis of Molecular Marker Data*, pp. 41-43. The initial cross gives rise to the F1 generation; the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" can also be referred to as a "linkage group".

The term "complement" refers to a nucleotide sequence that is complementary to a given nucleotide sequence, i.e. the sequences are related by the base-pairing rules.

The term "contiguous DNA" refers to overlapping contiguous genetic fragments.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A plant referred to herein as "diploid" has a paired set of chromosomes, in contrast to "haploid" which has a single set of chromosomes.

"Disease resistance" is a characteristic of a plant, wherein the plant avoids the disease symptoms that are the outcome of plant-pathogen interactions, such as maize-Et interactions. That is, pathogens are prevented from causing plant diseases and the associated disease symptoms, or alternatively, the disease symptoms caused by the pathogen are minimized or lessened. One of skill in the art will appreciate that the compositions and methods disclosed herein can be used with other compositions and methods available in the art for protecting plants from pathogen attack.

A plant referred to herein as a "doubled haploid" is developed by doubling the haploid set of chromosomes. A doubled haploid plant is considered a homozygous plant.

An "elite line" is any line that has resulted from breeding and selection for superior agronomic performance.

"Enhanced resistance" refers to an increased level of resistance against a particular pathogen, a wide spectrum of pathogens, or an infection caused by the pathogen(s). An increased level of resistance against a particular fungal pathogen, such as Et, for example, constitutes "enhanced" or improved fungal resistance. The embodiments of the invention will enhance or improve fungal plant pathogen resistance, such that the resistance of the plant to a fungal pathogen or pathogens will increase, which in turn, will increase resistance to the disease caused by the fungal pathogen. The term "enhance" refers to improve, increase, amplify, multiply, elevate, raise, and the like. Herein, plants of the invention are described as having "enhanced resistance" to *Exserohilum* and/or northern leaf blight infection, as a result of specific alleles at the locus of the invention.

"*Exserohilum turcicum*", previously referred to as *Helminthosporium turcicum*, is the fungal pathogen that induces northern leaf blight infection. The fungal pathogen is also referred to herein as *Exserohilum* or Et.

A "favorable allele" is the allele at a particular locus that confers, or contributes to, an agronomically desirable phenotype, e.g., enhanced resistance to *Exserohilum* and/or northern leaf blight, and that allows the identification of plants with that agronomically desirable phenotype. A "favorable" allele of a marker is a marker allele that segregates with the favorable phenotype.

"Fragment" is intended to mean a portion of a nucleotide sequence. Fragments can be used as hybridization probes or PCR primers using methods disclosed herein.

As used herein, "fungal resistance" refers to enhanced resistance or tolerance to a fungal pathogen when compared to that of a wild type plant. Effects may vary from a slight increase in tolerance to the effects of the fungal pathogen (e.g., partial inhibition) to total resistance such that the plant is unaffected by the presence of the fungal pathogen.

A "genetic map" is a description of genetic linkage relationships among loci on one or more chromosomes (or chromosomes) within a given species, generally depicted in a diagrammatic or tabular form. For each genetic map, distances between loci are measured by the recombination frequencies between them, and recombinations between loci can be detected using a variety of markers. A genetic map is a product of the mapping population, types of markers used, and the polymorphic potential of each marker between different populations. The order and genetic distances between loci can differ from one genetic map to another. For example, 10 cM on the internally derived genetic map (also referred to herein as "PHB" for Pioneer Hi-Bred) is roughly equivalent to 25-30 cM on the IBM2 2005 neighbors frame map (a high resolution map available on maizeGDB). However, information can be correlated from one map to another using a general framework of common markers. One of ordinary skill in the art can use the framework of common markers to identify the positions of markers and loci of interest on each individual genetic map. A comparison of marker positions between the internally derived genetic map and the IBM2 neighbors genetic map, for example, can be seen in Table 4.

The term "Genetic Marker" shall refer to any type of nucleic acid based marker, including but not limited to, Restriction Fragment Length Polymorphism (RFLP), Simple Sequence Repeat (SSR), Random Amplified Polymorphic DNA (RAPD), Cleaved Amplified Polymorphic Sequences (CAPS) (Rafalski and Tingey, 1993, *Trends in Genetics* 9:275-280), Amplified Fragment Length Polymorphism (AFLP) (Vos et al, 1995, *Nucleic Acids Res.* 23:4407-4414), Single Nucleotide Polymorphism (SNP) (Brookes, 1999, *Gene* 234:177-186), Sequence Characterized Amplified Region (SCAR) (Paran and Michelmore, 1993, *Theor. Appl. Genet.* 85:985-993), Sequence Tagged Site (STS) (Onozaki et al., 2004, *Euphytica* 138:255-262), Single Stranded Conformation Polymorphism (SSCP) (Orita et al., 1989, *Proc Natl Acad Sci USA* 86:2766-2770), Inter-Simple Sequence Repeat (ISSR) (Blair et al., 1999, *Theor. Appl. Genet.* 98:780-792), Inter-Retrotransposon Amplified Polymorphism (IRAP), Retrotransposon-Microsatellite Amplified Polymorphism (REMAP) (Kalendar et al., 1999, *Theor. Appl. Genet.* 98:704-711), an RNA cleavage product (such as a Lynx tag), and the like.

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to polymorphisms at a particular locus, such as a single marker locus, or polymorphisms at multiple loci along a chromosomal segment. The former can also be referred to "marker haplotypes" or "marker alleles", while the latter can be referred to as "long-range haplotypes".

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (BSSS) and "Lancaster" or "Lancaster Sure Crop" (sometimes referred to as NSS, or non-Stiff Stalk).

The term "heterozygous" means a genetic condition wherein different alleles reside at corresponding loci on homologous chromosomes.

The term "homozygous" means a genetic condition wherein identical alleles reside at corresponding loci on homologous chromosomes.

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

An "IBM genetic map" refers to any of following maps: IBM, IBM2, IBM2 neighbors, IBM2 FPC0507, IBM2 2004 neighbors, IBM2 2005 neighbors, or IBM2 2005 neighbors frame. IBM genetic maps are based on a B73×Mo17 population in which the progeny from the initial cross were randommated for multiple generations prior to constructing recombinant inbred lines for mapping. Newer versions reflect the addition of genetic and BAC mapped loci as well as enhanced map refinement due to the incorporation of information obtained from other genetic maps.

The term "inbred" refers to a line that has been bred for genetic homogeneity.

The term "indel" refers to an insertion or deletion, wherein one line may be referred to as having an insertion relative to a second line, or the second line may be referred to as having a deletion relative to the first line.

The term "introgression" or "introgressing" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background. For example, the chromosome 2 locus described herein may be introgressed into a recurrent parent that is not resistant or only partially resistant to Et and/or northern leaf blight. The recurrent parent line with the introgressed gene or locus then has enhanced resistance to Et and/or northern leaf blight.

The process of "introgressing" is often referred to as "backcrossing" when the process is repeated two or more times.

As used herein, the term "linkage" is used to describe the degree with which one marker locus is associated with another marker locus or some other locus (for example, a northern leaf blight resistance locus). The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same chromosome.) As used herein, linkage can be between two markers, or alternatively between a marker and a phenotype. A marker locus can be "associated with" (linked to) a trait, e.g., northern leaf blight resistance. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill, W. G. and Robertson, A, *Theor. Appl. Genet.* 38:226-231 (1968). When $r^2=1$, complete LD exists between the two marker loci, meaning that the markers have not been separated by recombination and have the same allele frequency. Values for $r^2$ above ⅓ indicate sufficiently strong LD to be useful for mapping (Ardlie et al., *Nature Reviews Genetics* 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome where a gene or marker is located.

The "logarithm of odds (LOD) value" or "LOD score" (Risch, *Science* 255:803-804 (1992)) is used in interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage.

"Maize" refers to a plant of the *Zea mays* L. ssp. *mays* and is also known as "corn".

The term "maize plant" includes: whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

A "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g. SSRs, RFLPs, FLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of maize molecular markers are known in the art, and are published or available from various sources, such as the Maize GDB internet resource and the Arizona Genomics Institute internet resource run by the University of Arizona.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele", alternatively an "allele of a marker locus", can refer to one of a plurality of polymorphic nucleotide sequences found at a marker locus in a population that is polymorphic for the marker locus.

"Marker assisted selection" (of MAS) is a process by which phenotypes are selected based on marker genotypes.

"Marker assisted counter-selection" is a process by which marker genotypes are used to identify plants that will not be selected, allowing them to be removed from a breeding program or planting.

A "marker haplotype" refers to a combination of alleles at a marker locus, e.g. PHM505 allele 2.

A "marker locus" is a specific chromosome location in the genome of a species where a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

"Northern leaf blight" (NLB), sometimes referred to as northern corn leaf blight (NCLB), is the disease caused by the pathogen *Exserohilum turcicum*. The disease is characterized by cigar-shaped lesions on leaf tissue and can have severe effects on yield, particularly in tropical climates or during wet seasons in temperate climates.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "phenotype", or "phenotypic trait" or "trait" refers to one or more trait of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

Each "PHM" marker represents two sets of primers (external and internal) that when used in a nested PCR, amplify a specific piece of DNA. The external set is used in the first round of PCR, after which the internal sequences are used for a second round of PCR on the products of the first round. This increases the specificity of the reaction. All of the PHM markers described herein are listed in Table 1, and the annealing temperature for these primers is 55° C. SNP markers were also developed for specific polymorphisms identified using the PHM markers and the nested PCR analysis (see, for example, PHM9343.12 in Tables 2 and 11). These SNP markers were specifically designed for use with the Invader® (Third Wave Technologies) platform.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA that is too common to be due merely to new mutation. A polymorphism must have a frequency of at least 1% in a population. A polymorphism can be a single nucleotide polymorphism, or SNP, or an insertion/deletion polymorphism, also referred to herein as an "indel".

The "probability value" or "p-value" is the statistical likelihood that the particular combination of a phenotype and the presence or absence of a particular marker allele is random.

Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

A "production marker" or "production SNP marker" is a marker that has been developed for high-throughput purposes. Production SNP markers were developed for specific polymorphisms identified using PHM markers and the nested PCR analysis. These production SNP markers were specifically designed for use with the Invader Plus® (Third Wave Technologies) platform.

The term "progeny" refers to the offspring generated from a cross.

A "progeny plant" is generated from a cross between two plants.

A "reference sequence" is a defined sequence used as a basis for sequence comparison. The reference sequence for a PHM marker, for example, is obtained by genotyping a number of lines at the locus, aligning the nucleotide sequences in a sequence alignment program (e.g. Sequencher), and then obtaining the consensus sequence of the alignment. Hence, a reference sequence identifies the polymorphisms in alleles at a locus. A reference sequence may not be a copy of an actual DNA sequence; however, it is useful for designing primers and probes for actual polymorphisms in the locus.

The "Stiff Stalk" heterotic group represents a major heterotic group in the northern U.S. and Canadian corn growing regions. It can also be referred to as the Iowa Stiff Stalk Synthetic (or BSSS) heterotic group.

A "topcross test" is a progeny test derived by crossing each parent with the same tester, usually a homozygous line. The parent being tested can be an open-pollinated variety, a cross, or an inbred line.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances.

An "unfavorable allele" of a marker is a marker allele that segregates with the unfavorable plant phenotype, therefore providing the benefit of identifying plants that can be removed from a breeding program or planting.

Longer sequences hybridize specifically at higher temperatures. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3, and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions are often: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32° C. and 48° C., depending on primer length. Additional guidelines for determining hybridization parameters are provided in numerous references. Sequence alignments and percent identity calculations may be determined using a variety of comparison methods designed to detect homologous sequences including, but not limited to, the MEGALIGN® program of the LASER-GENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS*. 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Turning now to the embodiments:

Genetic Mapping

It has been recognized for quite some time that specific genetic loci correlating with particular phenotypes, such as resistance to *Exserohilum* and/or northern leaf blight, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS). Such markers could also be used by breeders to design genotypes in silico and to practice whole genome selection.

A variety of methods well known in the art are available for detecting molecular markers or clusters of molecular markers that co-segregate with a trait of interest, such as resistance to *Exserohilum* and/or northern leaf blight. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

The present invention provides molecular marker loci that demonstrate statistically significant co-segregation with resistance to *Exserohilum* and/or northern leaf blight, as determined by association analyses and by traditional linkage mapping techniques. Detection of these marker loci or additional linked marker loci can be used in marker assisted maize breeding programs to produce plants with enhanced resistance to *Exserohilum* and/or northern leaf blight or to eliminate plants that do not have enhanced resistance to *Exserohilum* and/or northern leaf blight from breeding programs or planting.

Markers Associated with Resistance to *Exserohilum* and/or Northern Leaf Blight

Markers associated with resistance to *Exserohilum* and/or northern leaf blight are identified herein.

The marker locus can be selected from any of the PHM marker loci provided in Table 1 or Table 2, including the PHM markers PHM1784, PHM4743, PHM18704, PHM14460, PHM11925, PHM7853, PHM18903, PHM10887, PHM1868, PHM9218, PHM12722, PHM4828, PHM505, PHM8340, PHM9343, PHM2413, PHM12598, PHM2381, PHM4462, and PHM2109; the production SNP markers, PHM4743-50-A, PHM18903-29-A, PHM505-250-A, PHM8340-5-A, PHM2413-17-B, PHM9343-12-A, PHM9218-16-U, and PHM4828-12-U; and any marker linked to these markers (linked markers can be determined from the MaizeGDB resource; see Example 4 and Table 4).

Physical Map Location

The genetic elements or genes located on a contiguous linear span of genomic DNA on a single chromosome are physically linked.

PHM1784 and PHM2381, both highly associated with northern leaf blight resistance at a p-value ≤0.001, delineate a northern leaf blight resistance locus on the maize physical map (FIGS. 1A and 1B). Any polynucleotide that assembles to the contiguous DNA between and including SEQ ID NO:1 (the reference sequence for PHM1784), or a nucleotide sequence that is 95% identical to SEQ ID NO:1 based on the Clustal V method of alignment, and SEQ ID NO:20 (the reference sequence for PHM2381), or a nucleotide sequence that is 95% identical to SEQ ID NO:20 based on the Clustal V method of alignment, can house marker loci that are associated with the northern leaf blight resistance trait. FIGS. 1A and 1B show the physical map arrangement of the sequenced BACs that make up the contiguous stretch of DNA between and including PHM1784 and PHM2381. The gaps (represented by dotted lines) are not gaps in the contiguous stretch of DNA per se but are areas where BACs that have not been sequenced assemble to the physical map.

Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

Markers identified in Tables 1 and 2, as well as any marker within 50 cM of the markers identified in Tables 1 and 2, can be used to predict resistance to northern leaf blight in a plant. This includes any marker within 50 cM of the PHM markers, PHM1784, PHM4743, PHM18704, PHM14460, PHM11925, PHM7853, PHM18903, PHM10887, PHM1868, PHM9218, PHM12722, PHM4828, PHM505, PHM8340, PHM9343, PHM2413, PHM12598, PHM2381, PHM4462, and PHM2109, the markers associated with the northern leaf blight resistance trait at a p-level ≤0.001 in the association analysis, and the production SNP markers PHM4743-50-A, PHM18903-29-A, PHM505-250-A, PHM8340-5-A, PHM2413-17-B, PHM9343-12-A, PHM9218-16-U, and PHM4828-12-U.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can show co-segregation with the northern leaf blight resistance phenotype, it is important to note that the marker locus is not necessarily responsible for the expression of the northern leaf blight resistance phenotype. For example, it is not a requirement that the marker polynucleotide sequence be part of a gene that imparts enhanced northern leaf blight resistance (for example, be part of the gene open reading frame). The association between a specific marker allele and the enhanced northern leaf blight resistance phenotype is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

Chromosomal Intervals

Chromosomal intervals that correlate with northern leaf blight resistance are provided. These intervals are located on chromosome 2. Any marker located within these intervals finds use as a marker for northern leaf blight resistance. These intervals include:

(i) PHM1784 and PHM2381;

(ii) PHM18704 and PHM2381;

(iii) PHM18704 and PHM8340; and (iv) PHM10887 and PHM8340.

A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as markers for northern leaf blight resistance. Each of the intervals described above shows a clustering of markers that co-segregate with northern leaf blight resistance. This clustering of markers occurs in relatively small domains on the chromosomes, indicating the presence of a gene controlling the trait of interest in those chromosome regions. The intervals were drawn to encompass the markers that co-segregate with northern leaf blight resistance. The intervals are defined by the markers on their termini, where the interval encompasses markers that map within the interval as well as the markers that define the termini. For example, PHM1784 and PHM2381, separated by 6.3 cM on the internally-derived genetic map, define a chromosomal interval encompassing a cluster of markers that co-segregate with northern leaf blight resistance in the Stiff Stalk subpopulation at a p-level $\leq 0.001$ (FIG. 2). PHM18704 and PHM2381, separated by 6 cM on the internally-derived genetic map, define a chromosomal interval encompassing a cluster of markers that co-segregate with northern leaf blight resistance in the Stiff Stalk subpopulation at a p-level $\leq 1\times10^{-5}$. PHM18704 and PHM8340, separated by 3.4 cM on the internally-derived genetic map, define a chromosomal interval encompassing a cluster of markers that co-segregate with northern leaf blight resistance in the Stiff Stalk subpopulation at a p-level $\leq 1\times10^{-9}$. PHM10887 and PHM8340, separated by 0.5 cM on the internally-derived genetic map, define a chromosomal interval encompassing a cluster of markers that co-segregate with northern leaf blight resistance in the Stiff Stalk subpopulation at a p-level $\leq 1\times10^{-11}$. An interval described by the terminal markers that define the endpoints of the interval will include the terminal markers and any marker localizing within that chromosomal domain, whether those markers are currently known or unknown.

Chromosomal intervals can also be defined by markers that are linked to (show linkage disequilibrium with) a marker of interest, and $r^2$ is a common measure of linkage disequilibrium (LD) in the context of association studies. If the $r^2$ value of LD between any chromosome 2 marker locus lying within the interval of PHM1784 and PHM2381 and an identified marker within that interval that has an allele associated with enhanced resistance to *Exserohilum* and/or northern leaf blight is greater than ⅓ (Ardlie et al., *Nature Reviews Genetics* 3:299-309 (2002)), the loci are linked.

Marker Alleles and Haplotypic Combinations

A marker of the invention can also be a combination of alleles at one or more marker loci, otherwise known as a haplotype.

For example, there are two major haplotypes associated with enhanced resistance to *Exserohilum* and/or northern leaf blight in the Stiff Stalk heterotic group. One haplotype constitutes a "G" at PHM4743.50, a "G" at PHM18903.29, a "T" at PHM505.250, a "C" at PHM8340.5, a "G" at PHM2413.17, and a "C" at PHM9343.12, and the other haplotype constitutes an "A" at PHM4743.50, an "A" at PHM18903.29, a "T" at PHM505.250, a "T" at PHM8340.5, a "T" at PHM2413.17, and a "T" at PHM9343.12. Also identified herein is a haplotype associated with enhanced resistance to *Exserohilum* and/or northern leaf blight in a Non-Stiff Stalk heterotic group. This haplotype comprises an "A" at PHM18903.29, a "T" at PHM9218.16, and a "C" at PHM4828.12. In addition, one SNP, PHM4828.12, differentiates between the resistant lines PH4GP and PH1W2 and the susceptible lines PH5W4 and PH6WG as well as the resistant line PH8T0NL1 and the susceptible line PH8T0. The resistant lines have a "C" at PHM4828.12, while the susceptible lines have a "G". Marker allele PHM4828.12 could be used alone, or in combination with other marker alleles, to identify and select for maize plants with enhanced resistance to *Exserohilum* and/or northern leaf blight.

The skilled artisan would expect that there might be additional polymorphic sites at marker loci in and around the chromosome 2 markers identified herein, wherein one or more polymorphic sites is in linkage disequilibrium (LD) with an allele at one or more of the polymorphic sites in the haplotype. Two particular alleles at different polymorphic sites are said to be in LD if the presence of the allele at one of the sites tends to predict the presence of the allele at the other site on the same chromosome (Stevens, *Mol. Diag.* 4:309-17 (1999)).

Marker Assisted Selection

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in plant development, e.g. kernel characteristics. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors maps, which are available online on the MaizeGDB website.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide*. Academic press. pp 75-135).

Various types of SSR markers can be generated, and SSR profiles from resistant lines can be obtained by gel electrophoresis of the amplification products. Scoring of marker genotype is based on the size of the amplified fragment. An SSR service for maize is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; Bhattramakki and Rafalski (2001) Discovery and application of single nucleotide polymorphism markers in plants. In: R. J. Henry, Ed, *Plant Genotyping: The DNA Fingerprinting of Plants*, CABI Publishing, Wallingford. A wide range of commercially available technologies utilize these and other methods to interrogate SNPs including Masscode™ (Qiagen), Invader® (Third Wave Technologies), SnapShot® (Applied Biosystems), Taqman® (Applied Biosystems) and Beadarrays™ (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele 'T' for a specific line or variety with resistance to *Exserohilum* and/or northern leaf blight, but the allele 'T' might also occur in the maize breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

Many of the primers listed in Tables 1 or 2 can readily be used as FLP markers to select for the gene locus on chromosome 2 controlling resistance to northern leaf blight, owing to the presence of insertions/deletion polymorphisms. These primers can also be used to convert these markers to SNP or other structurally similar or functionally equivalent markers (SSRs, CAPs, indels, etc), in the same regions. One very productive approach for SNP conversion is described by Rafalski (2002a) *Current opinion in plant biology* 5 (2): 94-100 and also Rafalski (2002b) *Plant Science* 162: 329-333. Using PCR, the primers are used to amplify DNA segments from individuals (preferably inbred) that represent the diversity in the population of interest. The PCR products are sequenced directly in one or both directions. The resulting sequences are aligned and polymorphisms are identified. The polymorphisms are not limited to single nucleotide polymorphisms (SNPs), but also include indels, CAPS, SSRs, and VNTRs (variable number of tandem repeats). Specifically with respect to the fine map information described herein, one can readily use the information provided herein to obtain additional polymorphic SNPs (and other markers) within the region amplified by the primers listed in this disclosure. Markers within the described map region can be hybridized to BACs or other genomic libraries, or electronically aligned with genome sequences, to find new sequences in the same approximate location as the described markers.

In addition to SSR's, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

In general, MAS uses polymorphic markers that have been identified as having a significant likelihood of co-segregation with northern leaf blight resistance. Such markers are presumed to map near a gene or genes that give the plant its northern leaf blight resistance phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny.

The markers and intervals presented herein find use in MAS to select plants that demonstrate enhanced resistance to *Exserohilum* and/or northern leaf blight.

Methods for selection can involve obtaining DNA accessible for analysis, detecting the presence (or absence) of either an identified marker allele or an unknown marker allele that is linked to and associated with an identified marker allele, and then selecting the maize plant or germplasm based on the allele detected.

Marker alleles that can be assayed include: PHM4743-50-A, PHM18903-29-A, PHM505-250-A, PHM8340-5-A, PHM2413-17-B, PHM9343-12-A, PHM9218-16-U, and PHM4828-12-U.

Methods for selecting maize plants with enhanced resistance to *Exserohilum* and/or northern leaf blight can also involve detecting alleles at one or more marker loci lying within specific chromosomal intervals or assaying at least one marker locus within a specific chromosomal interval.

For instance, a maize plant having at least one allele of a marker locus lying within any of the following intervals:

(i) PHM1784 and PHM2381;

(ii) PHM18704 and PHM2381;

(iii) PHM18704 and PHM8340; and (iv) PHM10887 and PHM8340, wherein the allele is associated with enhanced resistance to *Exserohilum* and/or northern leaf blight, can be crossed to another maize plant, and a progeny plant arising from the cross can be evaluated for the marker allele and selected if the marker allele is present.

Haplotypes can also be used in MAS to introduce enhanced resistance to *Exserohilum* and/or northern leaf blight into susceptible maize lines or varieties. Three resistant haplotypes are presented herein. Haplotype 1 comprises a “G” at PHM4743.50, a “G” at PHM18903.29, a “T” at PHM505.250, a “C” at PHM8340.5, a “G” at PHM2413.17, and a “C” at PHM9343.12. Haplotype 2 comprises an “A” at PHM4743.50, an “A” at PHM18903.29, a “T” at PHM505.250, a “T” at PHM8340.5, a “T” at PHM2413.17, and a “T” at PHM9343.12. Haplotype 3 comprises an “A” at PHM18903.29, a “T” at PHM9218.16, and a “C” at PHM4828.12. Any allele that is in linkage disequilibrium with either of these three haplotypes can also be used in MAS to select plants with enhanced resistance to *Exserohilum* and/or northern leaf blight.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1

Phenotyping of Northern Leaf Blight Infection

Maize plants are evaluated on a 1 to 9 scale, where scores of 1-3 indicate "susceptible", scores of 4-6 indicate "intermediate", and scores of 7-9 indicate "resistant". The scoring diagram in FIG. 3 is used as a guide, with an emphasis placed on lesions above the ear. The lesions are verified as being caused by northern leaf blight infection by checking that the lesions are cigar or boat-shaped with smooth sides and/or by sending a sample to a diagnostic lab to confirm the identity of the pathogen.

At two to four weeks after flowering, scores are obtained from a few known susceptible lines and then compared to their historical scores. If the known susceptible lines rate at least two scores higher than their historical scores, scoring of the lines in the test set is delayed, thereby allowing the disease to advance to a standard state of infection. The scoring period can only be extended until prior to plant senescence. Thus, if the scores are still too high after 4-5 weeks, the disease pressure is insufficient for effective scoring.

If scores from the known susceptible lines do correlate with their historical scores in the time period from 2-4 weeks after flowering until prior to plant senescence, the test lines are scored on a plot basis using the scoring diagrams in FIG. 3 as a guide.

Example 2

Association Mapping Analysis

An association mapping strategy was undertaken to identify markers associated with northern leaf blight resistance in maize. In this association analysis, a collection of 475 maize lines was analyzed by DNA sequencing at 4000-10000 genes (genetic loci). The lines encompassed elite germplasm, commercially released cultivars, and other public varieties.

Northern leaf blight scores were obtained from the 475 individuals, as described in the previous example. One hundred and twenty-three lines with extreme phenotypes (scores of 1 or 9) were tested against genotypes in a whole genome association test (using 2×2 contingency tables with Fisher's exact test). A structure-based association analysis was used, where the population structure is controlled using marker data. The model-based cluster analysis software, Structure, developed by Pritchard et al., (*Genetics* 155:945-959 (2000)) was used with haplotype data for 880 elite maize inbreds at two hundred markers to estimate admixture coefficients and assign the inbreds to seven subpopulations. This reduces the occurrence of false positives that can arise due to the effect of population structure on association mapping statistics. Kuiper's statistic for testing whether two distributions are the same was used to test a given marker for association between haplotype and phenotype in a given subpopulation (Press et al., Numerical Recipes in C, second edition, Cambridge University Press, NY (2002)).

In one subpopulation, representing the Stiff Stalk heterotic group, a strong peak of significant marker-trait associations was identified on chromosome 2. The apex of this peak occurred at 201.4 cM on the internally derived genetic map (FIG. 2). Table 3 provides a listing of the maize markers significantly associated with northern leaf blight resistance at the p≤0.001 level (see boxed region in FIG. 2). Positions are given in cM, with position zero being the first (most distal from the centromere) marker known at the beginning of the chromosome. These map positions are not absolute, and represent an estimate of map position based on the internally derived genetic map.

TABLE 3

Markers significantly associated with northern leaf blight resistance at p ≤ 0.001 in the Stiff Stalk subpopulation

| Marker Locus | Reference Sequence | Relative map position (cM) PHB v1.4 | P-value |
|---|---|---|---|
| PHM1784 | SEQ ID NO: 1 | 197.8 | 7.40E−04 |
| PHM18704 | SEQ ID NO: 3 | 198.1 | 2.06E−10 |
| PHM14460 | SEQ ID NO: 4 | 198.7 | 1.97E−09 |
| PHM11925 | SEQ ID NO: 5 | 199.0 | 3.46E−07 |
| PHM7853 | SEQ ID NO: 6 | 199.0 | 3.29E−06 |
| PHM18903 | SEQ ID NO: 7 | 199.8 | 2.87E−07 |
| PHM10887 | SEQ ID NO: 9 | 201.0 | 8.32E−13 |
| PHM1868 | SEQ ID NO: 10 | 201.0 | 1.00E−11 |
| PHM9218 | SEQ ID NO: 11 | 201.0 | 2.18E−11 |
| PHM12722 | SEQ ID NO: 15 | 201.0 | 2.68E−10 |
| PHM4828 | SEQ ID NO: 8 | 201.0 | 7.36E−10 |
| PHM505 | SEQ ID NO: 12 | 201.4 | 3.02E−13 |
| PHM8340 | SEQ ID NO: 13 | 201.5 | 3.90E−13 |
| PHM12598 | SEQ ID NO: 19 | 203.8 | 2.02E−06 |
| PHM2381 | SEQ ID NO: 20 | 204.1 | 8.89E−07 |
| PHM4462 | SEQ ID NO: 17 | 204.4 | 4.14E−04 |
| PHM2109 | SEQ ID NO: 18 | 205.1 | 1.22E−07 |

Example 3

Fine Mapping of Northern Leaf Blight Resistance Locus

Two large backcross-derived populations were created for fine mapping using four of the lines used in the association analysis (example 2). Population 1 was created from a cross between resistant line PH1W2 (score=9) and susceptible line PH6WG (score=1), while population 2 was created from a cross between resistant line PH4GP (score=9) and susceptible line PH5W4 (score=1).

In each population, the susceptible line was used as the recurrent parent, and BC5 individuals were scored for northern leaf blight infection. Each of the individuals was genotyped at the following markers: PHM4743 (197.9), PHM18903 (199.8), PHM505 (201.4), PHM8340 (201.5), PHM9343 (202.3), and PHM2413 (203.0). (Numbers in parentheses indicate their genetic location on the internally derived PHB map.) For population 1, recombination data from 1250 individuals placed the gene in a region defined by markers PHM4743 and PHM9343. Recombination data from a larger set of individuals from population 2 (2450 individuals) placed the gene in the region defined by markers PHM18903 and PHM8340. The latter region covers a BAC interval bounded by and including BACs c0280 m20 and c0537d11 (See FIGS. 1A and 1B). The mapping of the resistance locus to the same (overlapping) interval in both populations suggests that the same gene is responsible for the resistant phenotype in PH1W2 and PH4GP.

The sequences of the ends of BACs in the interval, as well as ESTs known to be located on these BACs, were used to identify new markers with which to further narrow the range in which the locus was located. Phenotypic and genotypic correlations were made between the population 2 individuals and the additional set of markers, further delimiting the northern leaf blight gene locus to a physical map interval bounded by and including marker locus PHM505 and a low copy BAC end (from BAC b0199a06), representing a 254 kb interval, and then to an 18 kb region encompassing at least two candidate genes. (All BACs and BAC contigs described herein were derived from a B73 BAC library.)

Example 4

Markers within Interval and Use for Marker Assisted Selection

The positions of the markers identified in Examples 2 and 3 as being linked to the trait of interest can be located on a genetic and/or physical map, allowing the identification of other markers in the interval that could also be used for marker assisted selection. Table 4 shows PHM and public markers and their respective positions on both the PHB internally derived genetic map and the most current version of the IBM2 neighbors genetic map available on the maizeGDB website. The markers making up the interval are in bold print; the remaining markers are markers found to be associated with the ht1 resistance locus. The current physical map showing the physical map locations of the markers within the interval is also shown in FIGS. 1A and 1B.

TABLE 4

Molecular marker positions on the PHB map and the IBM2 Neighbors map

| Marker | Relative map position (cM) | Relative map position (cM) |
|---|---|---|
| Locus | PHB v1.4 | IBM2 |
| umc22a | n/a | 451.0 |
| ht1 | n/a | 504.0 |
| umc122a | n/a | 509.2 |
| csu920A | n/a | 524.7 |
| bnl6.20 | 195.5 | 529.8 |
| PHM1784 | 197.8 | 536.5 |
| PHM4743 | 197.9 | n/a |
| PHM18704 | 198.1 | 536.5 |
| PHM14460 | 198.7 | 536.5 |
| PHM11925 | 199.0 | 536.5 |
| PHM7853 | 199.0 | 536.5 |
| PHM18903 | 199.8 | 536.5 |
| chc101B | n/a | 537.2 |
| PHM12722 | 201.0 | n/a |
| PHM4828 | 201.0 | 538.8 |
| PHM10887 | 201.0 | n/a |
| PHM9218 | 201.0 | 538.8 |
| PHM1868 | 201.0 | 538.8 |
| ay109645 | 201.3 | 538.8 |
| PHM505 | 201.4 | n/a |
| PHM8340 | 201.5 | n/a |
| NPI298 | 202.1 | 548.3 |
| umc2085 | 202.3 | 544.4 |
| PHM9343 | 202.3 | n/a |
| PHI090 | 202.4 | 548.3 |
| umc1633 | 202.4 | 548.5 |
| PHM2413 | 203.0 | 536.5 |
| PHM12598 | 203.8 | n/a |

TABLE 4-continued

Molecular marker positions on the PHB map and the IBM2 Neighbors map

| Marker | Relative map position (cM) | Relative map position (cM) |
|---|---|---|
| mmp34 | 204.0 | 562.5 |
| PHM2381 | 204.1 | n/a |
| PHM4462 | 204.4 | n/a |
| umc1992 | n/a | 556.2 |
| PHM2109 | 205.1 | 565.9 |
| umc36 | n/a | 661.1 |

Closely linked markers flanking the locus of interest that have alleles in linkage disequilibrium with a resistance allele at that locus may be effectively used to select for progeny plants with enhanced resistance to Exserohilum and/or northern leaf blight. Thus, the markers described herein, such as those listed in Tables 1 and 2, as well as other markers genetically or physically mapped to the same chromosomal segment, may be used to select for maize plants with enhanced resistance to Exserohilum and/or northern leaf blight. Typically, a set of these markers will be used, (e.g., 2 or more, 3 or more, 4 or more, 5 or more) in the flanking region above the gene and a similar set in the flanking region below the gene. Optionally, as described above, a marker within the actual gene and/or locus may also be used. The parents and their progeny are screened for these sets of markers, and the markers that are polymorphic between the two parents are used for selection. The most proximal polymorphic markers to the gene or locus are used to select for the gene or locus, and the more distal polymorphic markers are used to select against the gene or locus. In an introgression program, this allows for selection of the gene or locus genotype at the more proximal polymorphic markers and selection for the recurrent parent genotype at the more distal polymorphic markers.

All plants to be used in the breeding program, such as a gene introgression program, are screened with markers. The markers disclosed herein or equivalent markers on the same chromosomal segment may be used.

Example 5

Haplotype Identification and Proprietary Stiff Stalk Germplasm Survey

Plant haplotypes, either at specific marker loci or at multiple marker loci, that are associated with enhanced resistance to Exserohilum and/or northern leaf blight can be used to identify resistant individuals. Primer pairs for the PHM markers listed in Table 1 can be used to identify marker haplotypes, for instance, using a nested PCR reaction. The external primer pairs for PHM4743, PHM18903, PHM505, PHM8340, PHM2413, and PHM9343, for example, were used to amplify the genomic DNA from a set of maize lines. In this first PCR reaction, 0.90 µl of 10×PCR buffer, 0.18 µl of 10 mM dNTP mix, 0.27 µl of 50 mM MgCl$_2$, 1.50 µl of 2.5 µM external forward primer, 1.50 µl of 2.5 µM external reverse primer, 0.04 µl of Platinum Taq, 1.61 µl of ddH2O, and 3 µl of 1.5 ng/µl DNA were used. The thermocycling conditions constituted: 95° C. at 5 minutes; 94° C. for 20 seconds, 55° C. for 30 seconds, and 72° C. for 2 minutes, repeated for 24 cycles; 72° C. for 10 minutes; and a hold at 4° C. The DNA produced from the first round of PCR was then diluted 1:9 with TE for use in the second round of PCR. The reaction mix for the second round of PCR was the same except the internal primers were used. The thermocycling conditions for the second round of PCR constituted: 95° C. at 5 minutes; 94° C. for 20 seconds, 55° C. for 30 seconds, and 72° C. for 2 minutes, repeated for 28 cycles; 72° C. for 10 minutes; and a hold at 4° C. The resulting PCR fragments were sequenced in the forward and reverse direction, and the sequences were aligned to give a reference sequence (see the sequences set forth in SEQ ID NOs: 2, 7, 12, 13, 14, and 16). SNPs and indels were then identified. Tables 6-11 show the marker alleles, or marker haplotypes, that occur in the proprietary germplasm at a frequency greater than 1%.

Marker alleles can be interrogated by sequencing the fragment or by designing markers to each SNP or indel within a fragment. Markers were designed for the following SNPs for use with the Invader™ technology: PHM4743.50, PHM18903.29, PHM505.250, PHM8340.5, PHM2413.17, and PHM9343.12 (See polymorphisms marked with an asterisk in Tables 6-11). Invader™ (Third Wave Technologies, Madison, Wis.) markers were designed using segments from each of the reference sequences. Primers were designed around each probe site to give an amplicon size below 150 bp. Markers indicated the presence of a particular allele with fluorescence due to hybridization, with the absence of the allele resulting in no fluorescence. A control fluorescence signal was also generated by designing a marker that hybridizes to a second highly conserved maize gene, so that the presence of a specific allele results in fluorescence of two dyes and the absence results in fluorescence due to the conserved gene only. This 'control' florescence was used to reduce lab error by distinguishing between the situations where the allele is in fact absent and the situation where a false negative has occurred because of a failed reaction. Hence, as in Table 2, probes designated as "1" were used for allele "1", and probes designated as "2" were used for allele "2".

Each of these SNPs (PHM4743.50, PHM18903.29, PHM505.250, PHM8340.5, PHM2413.17, and PHM9343.12) was typed in resistant plants from both biparental mapping populations, thereby assaying a "long-range haplotype". PH4GP and PH1W2, had distinct "long-range" haplotypes, which were identified as being derived from different founders. Table 5 shows the long-range haplotypes for PH4GP, PH1W2, PH5W4, and PH6WG.

TABLE 5

PH4GP, PH1W2, PH5W4, and PH6WG haplotypes

| Haplotype | Phenotypic Score | PHM4743.50 | PHM18903.29 | PHM505.250 | PHM8340.5 | PHM9343.12 | PHM2413.17 |
|---|---|---|---|---|---|---|---|
| PH4GP | 9 | A | A | T | T | T | T |
| PH1W2 | 9 | G | G | T | C | C | G |
| PH5W4 | 1 | A | G | C | C | T | T |
| PH6WG | 1 | A | G | H | C | T | T |

In addition, seven hundred fifty three Stiff Stalk lines from a proprietary North American germplasm pool were screened for resistance to northern leaf blight. Five hundred forty lines did not have either of the two resistant haplotypes, while one hundred eighty seven had one of the two resistant haplotypes. Ninety had the haplotype of line PH1W2 at SNP loci PHM4743.50, PHM18903.29, PHM505.250, PHM8340.5, PHM2413.17, and PHM9343.12, while ninety seven had the PH4GP haplotype. The haplotypes of the remaining twenty six were inconclusive.

TABLE 6

PHM4743 Polymorphisms

| Nucleotide position on SEQ ID NO: 2 | PHM4743.9 | PHM4743.14 | PHM4743.18 | PHM4743.19 |
|---|---|---|---|---|
| Type Marker | 299 | 311 | 335 | 353 |
| Allele | SNP | SNP | SNP | SNP |
| 4 | C | C | G | T |
| 1 | C | C | A | C |
| 5 | T | C | A | C |
| 3 | C | C | A | C |
| 6 | C | T | A | C |
| 2 | C | C | A | C |
| 10 | C | C | A | C |
| 9 | C | C | A | C |

| Nucleotide position on SEQ ID NO: 2 | PHM4743.23 | PHM4743.24 | PHM4743.3 | PHM4743.26 |
|---|---|---|---|---|
| Type Marker | 387 | 388 | 405 | 415 |
| Allele | SNP | SNP | DEL | SNP |
| 4 | C | G | W | C |
| 1 | C | G | W | C |
| 5 | C | G | W | C |
| 3 | C | G | W | A |
| 6 | C | G | M | C |
| 2 | A | G | W | C |
| 10 | T | T | W | C |
| 9 | T | T | W | C |

| Nucleotide position on SEQ ID NO: 2 | PHM4743.1 | PHM4743.28 | PHM4743.30 | PHM4743.33 |
|---|---|---|---|---|
| Type Marker | 425 | 427 | 433 | 442 |
| Allele | DEL | SNP | SNP | SNP |
| 4 | W | A | C | G |
| 1 | W | A | C | A |
| 5 | W | A | C | A |
| 3 | M | C | C | A |
| 6 | M | C | C | A |
| 2 | W | A | C | A |
| 10 | W | A | C | G |
| 9 | W | A | T | G |

| Nucleotide position on SEQ ID NO: 2 | PHM4743.37 | PHM4743.39 | PHM4743.40 | PHM4743.42 |
|---|---|---|---|---|
| Type Marker | 449 | 462 | 468 | 474 |
| Allele | SNP | SNP | SNP | SNP |
| 4 | T | T | C | T |
| 1 | T | T | C | T |
| 5 | A | T | C | T |
| 3 | A | T | G | T |
| 6 | A | G | G | C |
| 2 | A | T | C | T |
| 10 | T | T | C | T |
| 9 | T | T | C | T |

TABLE 6-continued

PHM4743 Polymorphisms

| Nucleotide position on SEQ ID NO: 2 | PHM4743.5 | PHM4743.47 | PHM4743.48 | PHM4743.50* |
|---|---|---|---|---|
| Type Marker | 495 | 504 | 524 | 554 |
| Allele | DEL | SNP | SNP | SNP |
| 4 | W | C | C | A |
| 1 | M | C | T | G |
| 5 | M | T | C | G |
| 3 | M | C | C | G |
| 6 | M | C | C | A |
| 2 | M | C | C | G |
| 10 | M | C | C | A |
| 9 | M | C | C | A |

M = differs from reference sequence, SEQ ID NO: 2
W = same as reference sequence, SEQ ID NO: 2

TABLE 7

PHM18903 Polymorphisms

| Nucleotide position on SEQ ID NO: 7 | PHM18903.12 | PHM18903.13 | PHM18903.14 | PHM18903.15 | PHM18903.29* | PHM18903.43 | PHM18903.45 |
|---|---|---|---|---|---|---|---|
| Type Marker Allele | 167 SNP | 169 SNP | 181 SNP | 218 SNP | 360 SNP | 388 SNP | 419 SNP |
| 5 | C | G | T | T | A | T | T |
| 1 | C | G | T | T | G | T | A |
| 3 | C | G | T | G | G | T | A |
| 8 | C | G | T | T | G | T | T |
| 2 | C | G | T | T | A | C | A |
| 7 | A | G | T | G | A | C | A |
| 11 | C | A | C | G | A | C | A |

TABLE 8

PHM505 Polymorphisms

| Nucleotide position in SEQ ID NO: 12 | PHM505.225 | PHM505.197 | PHM505.234 | PHM505.199 |
|---|---|---|---|---|
| Type Marker | 50 | 86 | 91 | 116 |
| Allele | SNP | INS | SNP | INS |
| 1 | T | W | A | W |
| 3 | C | W | G | W |
| 7 | C | M | G | W |
| 5 | C | W | G | M |
| 2 | T | W | G | M |
| 8 | T | W | A | W |

| Nucleotide position in SEQ ID NO: 12 | PHM505.238 | PHM505.250* | PHM505.294 | PHM505.256 |
|---|---|---|---|---|
| Type Marker | 119 | 234 | 260 | 281 |
| Allele | SNP | SNP | INDEL | SNP |
| 1 | G | T | W | C |
| 3 | A | C | W | G |
| 7 | G | C | M | D |
| 5 | G | T | W | G |
| 2 | G | C | W | G |
| 8 | G | C | W | G |

| Nucleotide position in SEQ ID NO: 12 | PHM505.218 | PHM505.260 | PHM505.261 | PHM505.263 |
|---|---|---|---|---|
| Type Marker | 302 | 337 | 341 | 351 |
| Allele | INS | SNP | SNP | SNP |
| 1 | W | G | A | A |
| 3 | W | G | A | A |
| 7 | W | G | A | G |
| 5 | M | G | G | A |
| 2 | W | C | A | A |
| 8 | W | C | A | A |

| Nucleotide position in SEQ ID NO: 12 | PHM505.295 | PHM505.266 | PHM505.268 | PHM505.277 |
|---|---|---|---|---|
| Type Marker | 357 | 363 | 371 | 398 |
| Allele | INDEL | SNP | SNP | SNP |
| 1 | W | G | C | C |
| 3 | W | A | C | C |
| 7 | W | G | C | C |
| 5 | W | A | G | T |
| 2 | M | D | D | D |
| 8 | M | D | D | D |

| Nucleotide position in SEQ ID NO: 12 | PHM505.200 | PHM505.279 | PHM505.296 | PHM505.286 |
|---|---|---|---|---|
| Type Marker | 406 | 410 | 416 | 421 |
| Allele | INS | SNP | INDEL | SNP |
| 1 | W | C | W | C |
| 3 | W | C | W | C |
| 7 | W | T | W | A |
| 5 | W | C | M | D |
| 2 | D | D | D | D |
| 8 | D | D | D | D |

M = differs from reference sequence, SEQ ID NO: 12
W = same as reference sequence, SEQ ID NO: 12
D = deleted nucleotide

TABLE 9

PHM8340 Polymorphisms

| Nucleotide position on SEQ ID NO: 13 | PHM8340.2 | PHM8340.3 | PHM8340.4 | PHM8340.5* |
|---|---|---|---|---|
| Type Marker | 116 | 163 | 205 | 227 |
| Allele | SNP | SNP | SNP | SNP |
| 4 | C | A | G | C |
| 1 | G | C | G | T |

TABLE 9-continued

PHM8340 Polymorphisms

| Nucleotide position on SEQ ID NO: 13 Type Marker Allele | PHM8340.2 116 SNP | PHM8340.3 163 SNP | PHM8340.4 205 SNP | PHM8340.5* 227 SNP |
|---|---|---|---|---|
| 2 | G | C | G | C |
| 3 | G | C | A | C |

TABLE 10

PHM2413 Polymorphisms

| Nucleotide position in SEQ ID NO: 14 Type Marker allele | PHM2413.9 87 SNP | PHM2413.12 228 SNP | PHM2413.14 252 SNP | PHM2413.15 260 SNP | PHM2413.17* 336 SNP |
|---|---|---|---|---|---|
| 1 | C | C | A | G | T |
| 3 | C | C | A | G | G |
| 2 | G | A | G | A | G |

TABLE 11

PHM9343 Polymorphisms

| Nucleotide position on SEQ ID NO: 16 Type Marker Allele | PHM9343.2 94 DEL | PHM9343.1 96 DEL | PHM9343.8 160 SNP | PHM9343.9 172 SNP | PHM9343.12* 320 SNP | PHM9343.14 386 SNP |
|---|---|---|---|---|---|---|
| 2 | W | W | C | G | T | C |
| 1 | M | D | C | G | T | C |
| 7 | W | W | C | G | C | A |
| 4 | W | M | C | T | T | C |
| 5 | M | D | T | G | T | C |
| 3 | W | M | C | G | T | C |

M = differs from reference sequence, SEQ ID NO: 16
W = same as reference sequence, SEQ ID NO: 16
D = deleted nucleotide Example 6

Backcrossing Favorable Alleles/Haplotypes into Susceptible Lines

A Stiff Stalk inbred with enhanced resistance to *Exserohilum* and/or northern leaf blight, as a result of having an identified resistant haplotype in the chromosome 2 region (such as in Table 5), can be crossed to a susceptible inbred (also the recurrent parent in a backcross), thereby producing an F1 population. F1 plants can then be backcrossed once more to the recurrent parent, resulting in a BC1 population. Seedlings can be planted out and backcrossed again to the recurrent parent to develop a BC2 population. DNA can then be prepared from leaf punches of BC2 families.

To determine which BC2 families to plant for further backcrosses, genotyping can be carried out on DNA from BC2 families using markers in the region of interest. Seeds from BC2 families can be planted and individual plants genotyped again for the presence of the introgressed resistance locus using the same markers noted above. Positive plants can be backcrossed to the recurrent parent once more to develop BC3 populations.

Example 7

Introgressing Resistance into a Susceptible Non-Stiff Stalk Line

PHK46 is a non-stiff stalk (NSS) line with a historical Northern leaf blight (NLFBLT) score of 6.5, while PH8T0 is a non-stiff stalk line with a historical NLFBLT score of 3.3. PHK46 has an "A" at PHM18903.29, a "T" at PHM9218.16, and a "C" at PHM4828.12, while PH8T0 has a "G" at PHM18903.29, a "C" at PHM9218.16, and a "G" at PHM4828.12. The two lines were crossed, and the progeny were subsequently backcrossed to PH8T0. Backcrossing to the PH8T0 parent ensued for 5 more generations, and marker assisted selection (MAS) was used to select for the PHK46 haplotype at the chromosome 2 locus in each generation. The resulting inbred was named PH15J51.

PH8T0 and PH15J51 were grown at eight locations with 2 reps per location across two years. Maize plants were evaluated for Northern leaf blight, based on a scale of 1 to 9 (see scoring diagram in FIG. 3). PH8T0 had an average NLFBLT score of 3.3, while PH15J51 had an average NLFBLT score of 6.7. This difference was significant at a p-value of 0.0001.

PH8T0 and PH15J51 were test crossed to three different inbreds, PH8JV, PHE6Z, and PHNAR, and the resulting hybrids were compared in 2 yield test locations, with 2 replications per location. The NLFBLT tolerant versions of the hybrids were found to have increased disease tolerance compared to the non-tolerant versions. PH8JV/PH8T0 (wild-type) has a NLFBLT score of 4.8 compared to PH8JV/PH15J51 which has a score of 6.3. PHE6Z/PH8T0 (wild-type) has a NLFBLT score of 5.0 compared to PHE6Z/PH15J51 which has a score of 6.8. PHNAR/PH8T0 (wild-type) has a NLFBLT score of 4.5 compared to PHNAR/PH15J51 which has a score of 6.8. The difference across all crosses was significant at a p-value of 0.001.

What is claimed:

1. A method of identifying a maize plant that displays resistance to *Exserohilum* and/or northern leaf blight, the method comprising:
   A. isolating nucleic acids from a maize plant;
   B. analyzing the isolated nucleic acids for the presence of a haplotype associated with resistance to *Exserohilum* and/or northern leaf blight, wherein said haplotype is located within a chromosomal interval comprising and flanked by PHM1784 and PHM2381 and comprises:
   i. a "G" at PHM4743.50; a "G" at PHM18903.29; a "C" at PHM8340.5; and a "C" at PHM9343.12; or
   ii. an "A" at PHM4743.50; an "A" at PHM18903.29; a "T" at PHM8340.5; and a "T" at PHM9343.12; and
   C. selecting the maize plant if haplotype (i) or haplotype (ii) is detected.

2. A method of marker assisted selection comprising:
   A. obtaining a first maize plant that displays resistance to *Exserohilum* and/or northern leaf blight, wherein said maize plant has a haplotype within a chromosomal interval comprising and flanked by PHM1784 and PHM2381 said haplotype comprising:
   i. a "G" at PHM4743.50; a "G" at PHM18903.29; a "C" at PHM8340.5; and a "C" at PHM9343.12; or
   ii. an "A" at PHM4743.50; an "A" at PHM18903.29; a "T" at PHM8340.5; and a "T" at PHM9343.12;
   B. crossing said first maize plant to a second maize plant;
   C. evaluating the progeny for haplotype (i) or haplotype (ii); and
   D. selecting progeny plants that possess haplotype (i) or haplotype (ii) of the first maize plant.

* * * * *